(12) United States Patent
Rearick et al.

(10) Patent No.: US 7,008,887 B2
(45) Date of Patent: Mar. 7, 2006

(54) CELLULOSIC SUBSTRATES WITH REDUCED ABSORBENT CAPACITY HAVING THE CAPABILITY TO WICK LIQUIDS

(75) Inventors: William A. Rearick, Cary, NC (US); Birgit Andersen, Raleigh, NC (US)

(73) Assignee: Cotton Incorporated, Cary, NC (US)

( * ) Notice: Subject to any disclaimer, the term of this patent is extended or adjusted under 35 U.S.C. 154(b) by 433 days.

(21) Appl. No.: 09/969,293

(22) Filed: Sep. 28, 2001

(65) Prior Publication Data

US 2002/0064639 A1     May 30, 2002

Related U.S. Application Data

(60) Provisional application No. 60/237,090, filed on Sep. 29, 2000.

(51) Int. Cl.
  *B32B 27/04* (2006.01)
  *B32B 27/12* (2006.01)
  *B32B 5/02* (2006.01)

(52) U.S. Cl. .............................. 442/79; 442/81; 442/82; 442/187; 442/211; 442/307; 442/86; 442/181; 428/365; 428/393; 428/364; 428/375; 428/292.1

(58) Field of Classification Search .................. 442/79, 442/81–82, 187, 211, 307, 86, 181; 428/365, 428/393, 364, 375, 292.1
See application file for complete search history.

(56) References Cited

U.S. PATENT DOCUMENTS

| | | | |
|---|---|---|---|
| 3,250,095 A | | 5/1966 | Bird |
| 3,529,600 A | * | 9/1970 | Seltzer ........................ 604/370 |
| 3,838,692 A | | 10/1974 | Levesque |
| 4,501,025 A | | 2/1985 | Kuznetz |
| 4,615,188 A | * | 10/1986 | Hursh et al. ................... 66/196 |
| 4,735,843 A | * | 4/1988 | Noda .......................... 428/137 |
| 4,804,378 A | | 2/1989 | Shiba et al. |
| 5,065,600 A | * | 11/1991 | Byles ........................... 66/193 |
| 5,136,761 A | * | 8/1992 | Sternlieb et al. .............. 28/104 |
| 5,508,098 A | * | 4/1996 | Omar et al. ................. 442/319 |
| 5,511,323 A | * | 4/1996 | Dahlgren ..................... 36/3 A |
| 5,622,584 A | | 4/1997 | Kroyer |
| 5,759,662 A | | 6/1998 | Heiman |
| 5,888,914 A | * | 3/1999 | Katz .......................... 442/184 |
| 5,896,758 A | * | 4/1999 | Rock et al. ................... 66/191 |
| 5,901,373 A | | 5/1999 | Dicker |
| 5,990,377 A | | 11/1999 | Chen et al. |
| 6,151,928 A | * | 11/2000 | Anyon et al. ................. 66/196 |

FOREIGN PATENT DOCUMENTS

EP          0 429 802 A2    6/1991

(Continued)

OTHER PUBLICATIONS

Chemical Abstracts, vol. 135, No. 21, Abstract No. 305147z, Nov. 19, 2001.
XP002216157, Derwent Publications Ltd., London, Great Britain, Database WPI, Section Ch, Week 199913, AN 1999-149135, PN—JP11012924A.

(Continued)

*Primary Examiner*—Norca Torres

(57) ABSTRACT

The present invention relates to cellulosic substrates with reduced absorbent capacity having the capability to wick liquids, as well as to methods of manufacturing such cellulosic substrates. The cellulosic substrates provided by the present invention comprise an inside and an outside connected to the inside. The inside comprises cellulosic fibers and has a reduced absorbent capacity, and the outside comprises cellulosic fibers. The outside may have a reduced absorbent capacity and may have an absorbent capacity higher than the inside. The cellulosic substrate is capable of wicking liquid contacting the inside of the substrate to the outside of the substrate.

5 Claims, 4 Drawing Sheets

FOREIGN PATENT DOCUMENTS

| | | |
|---|---|---|
| EP | 0 496 567 A2 | 7/1992 |
| EP | 0 997 576 A2 | 5/2000 |
| GB | 739172 A | 10/1955 |
| JP | 60-94682 | 5/1985 |
| JP | 62-57983 | 3/1987 |
| JP | 06257073 A * | 9/1994 |
| JP | 11 012924 A | 1/1995 |
| JP | 2001-288651 | 10/2001 |
| WO | WO 98 56326 A1 | 12/1998 |
| WO | WO 00 19949 A1 | 4/2000 |

OTHER PUBLICATIONS

Dagenhart, Gary S. et al., "Hydrophilic Finishes for Synthetics and Cotton Blends", AATCC Functional Finishes and High Performance Textile Symposium, University Hilton, Charlotte, NC, Jan. 27-28, 2000.

Klaska, Frantisek et al., "Baby Diapers in Y2K—the challenge for nonwovens industry continues", Nonwovens Markets, Oct. 9, 2000, Miller Freeman, Inc.

English Translation of JP 60-94682, Kokoku H4-28830.

English Translation of JP 62-57983, Kokoku H1-53394.

* cited by examiner

Gross Absorbency Test
% Wet Pick Up Water

Printed vs. ctrl. (sponge w/ chamois) before HL

Gross Absorbency Test
% less WP of FC printed fabric

Printed vs. ctrl. before & after 1 HL (100% Cotton)

CELLULOSIC SUBSTRATES WITH REDUCED ABSORBENT CAPACITY HAVING THE CAPABILITY TO WICK LIQUIDS

RELATED APPLICATIONS

This application claims the priority benefit of U.S. Provisional Application No. 60/237,090, filed on Sep. 29, 2000, entitled "Recreational Performance Apparel," the entire content of which is hereby incorporated by reference.

FIELD OF THE INVENTION

The present application relates to cellulosic substrates with reduced absorbent capacity capable of wicking liquid as well as methods of preparing the same.

BACKGROUND OF THE INVENTION

Cotton is used in many products due to its many desirable characteristics. For example, cotton is used in absorbent products due to its high absorbency and is used in wearing apparel due in part to its many comfort properties (such as, for example, the natural moisture regain of cotton fibers and the moisture vapor transport and air permeability/breathability of fabrics made from cotton). However, some of the properties of cotton make its use undesirable in certain products.

For example, cotton has not traditionally been preferred for use in "recreational performance apparel" primarily due to its high absorbency. "Recreational performance apparel," as defined herein, is any apparel that is recommended for use during activities that may involve perspiration. For any fabric to perform in such garments, the moisture must be wicked "away from the skin" (i.e., the moisture must be transported away from the skin to the outside of the garment where it is dispersed). The moisture must in fact be absorbed by the fabric (i.e., pass through the fabric in the Z direction as well as spread or wick in the X and Y directions) whereby the outer layer or outside of the garment becomes wet and evaporation can occur. The same wicking effect must occur in a layered clothing system when perspiration occurs, as the liquid moisture must pass from an inside layer to an intermediate or outer layer whereby it eventually can evaporate.

The high absorbency of cotton translates into a variety of problems when used in garments where the consumer undertakes activities generating moderate or heavy perspiration for prolonged periods. These problems are that the garment gets too wet and heavy, sags due to the water weight, takes too long to dry, and sticks to the skin. Since skin is hydrophilic and the inside of the cotton fabric is hydrophilic, there is an interfacial/surface tension which forms at the skin/perspiration interface and at the fiber/perspiration interface. The interfacial tension combined with the surface tension of the water or perspiration cause the garment to stick to the skin when wet. This leads to discomfort and restricts the freedom of movement, which can be especially bad during athletic activity. Wet cotton fabrics can also make the wearer feel cold, especially after exercise or when moving into an air conditioned environment. The slow drying may allow more time for odors to build up due to bacterial action on the perspiration.

An alternative to using cotton in recreational performance apparel is to use hydrophobic synthetic fibers in the apparel. A variety of treatment chemistries are commercially available that can be used to produce wicking of liquid moisture in normally hydrophobic thermoplastic synthetic garments. (See, e.g., Reference paper on wicking finishes by Hodgson Chemical given at the AATCC Functional Finishes and High Performance Textile Symposium, University Hilton, Charlotte, N.C., Jan. 27–Jan. 28, 2000). The wicking finishes do not penetrate into typical hydrophobic synthetic fibers such as polyester. They are very hydrophilic and some can absorb up to 200 times their weight in water. These treatments do allow wicking of liquid moisture in otherwise non-absorbing fabrics. Garments made from these treated fabrics have become popular, as evidenced by products such as very thin polyester T shirts with a wicking finish.

The disadvantages of products like polyester shirts with wicking finishes are that they do not provide the same level of comfort to the wearer during periods of non-exertion as cotton garments. Polyester absorbs almost no water within the fiber and tends to feel clammy when relatively low levels of liquid moisture are present, because the moisture is present on the surface of the fibers. In addition, many synthetic garments suffer from odor retention problems.

There are also treatment chemistries available that are used to provide water repellency or other hydrophobic properties to cotton and/or other hydrophilic fibers. These include, for example, waxes, silicones, and fluorochemicals. Such chemicals are typically applied by padding, the goal of which is to saturate and distribute the chemical finishes uniformly throughout the fabric in all directions. Tightly woven cotton fabrics treated with such compounds can be used for raincoats or awnings. However, when used for recreational performance apparel, perspiration is not wicked away, but rather collects between the skin and the fabric, which can be highly uncomfortable to the wearer.

Synthetic fabrics are also typically preferred over cotton fabrics for certain recreational performance apparel applications because most cotton garments (such as t-shirts and running shorts) that are used for certain athletic activities are relatively thick and heavy (i.e., the fabrics have a high area density) compared to many of their synthetic counterparts. The cotton fabrics used in these garments are thicker than their synthetic counterparts because of the physical properties of the fibers, filaments, and the yarns used to produce them. The increased thickness of the cotton garments further aggravates the moisture management issues because thicker fabrics absorb more moisture (i.e., have a higher absorbent capacity), get heavier, and take longer to dry. Thicker fabrics, with other variables held constant, have more internal capillary spaces which hold liquid than do thinner fabrics.

Cotton has also not been preferred in some absorbent products that are worn next to the skin. For example, cotton has not been preferred in the topsheets of adult and baby diapers and sanitary napkins. (The topsheet is the part of an absorbent disposable diaper or sanitary napkin which touches the skin of the user and which is typically a nonwoven fabric.) Urine or menstrual fluid must pass through the topsheet and into an absorbent core where it is trapped. In order to maximize the comfort of the user of such a product, it is desirable to maximize the wicking of liquid in the Z direction (i.e., the direction normal to the plane of the fabric) and away from the skin. The ideal scenario is for the topsheet to stay dry.

Polypropylene nonwovens have established themselves as the most common topsheet material. Although polypropylene is a relatively inexpensive fiber, it is not widely used in general wearing apparel that is to be worn next to the skin. This is because polypropylene is not as comfortable as cotton, because polypropylene is not readily dyeable, and because polypropylene adsorbs and holds odors. Furthermore, polypropylene may tend to exacerbate skin irritation. (See, e.g., Baby Diapers in Y2K—the challenge for the nonwovens industry continues, Nonwoven Markets, Oct. 9, 2000, Miller Freeman Inc.)

Disposable diapers, sanitary napkins, and any absorbent products that use polypropylene next to the skin are lacking in basic comfort properties in comparison to products that have cotton next to the skin. In the dry state (i.e., prior to urination during use), a topsheet made from regular bleached cotton fiber would benefit the wearer by providing the many comfort properties of cotton. However, a topsheet made of 100% regular bleached cotton would tend to hold too much urine (or menstrual fluid) next to the skin.

It would be advantageous to provide products prepared from cotton or other cellulosic materials which have reduced absorbent capacity but include wicking properties. The present invention provides such products as well as methods of manufacturing such products.

SUMMARY OF THE INVENTION

The present invention relates to cellulosic substrates with reduced absorbent capacity having the capability to wick liquids, as well as to methods of manufacturing such cellulosic substrates. In one aspect of the present invention, a cellulosic substrate is provided comprising an inside and an outside connected to the inside. The inside comprises cellulosic fibers and has a reduced absorbent capacity, and the outside comprises cellulosic fibers. The cellulosic substrate is capable of wicking liquid contacting the inside of the substrate to the outside of the substrate.

In another aspect of the present invention, an absorbent product is provided comprising a topsheet and an absorbent core. The topsheet comprises cellulosic fibers and has a reduced absorbent capacity. The topsheet also has an inside surface for contacting a user's skin and an outside surface. The absorbent core is adjacent to the outside surface of the topsheet and has an absorbent capacity higher than the topsheet. The absorbent product is capable of wicking liquid contacting the inside surface of the topsheet to the core.

A further aspect of the present invention provides a method of forming a cellulosic substrate having a reduced absorbent capacity and capable of wicking liquid. A cellulosic substrate is provided that has an inside and an outside. A hydrophobic treatment material is applied to the inside of the substrate in a discontinuous manner such that the inside of the substrate has an absorbent capacity lower than the outside and such that the substrate is capable of wicking liquid contacting the inside of the substrate to the outside of the substrate.

Another aspect of the present invention provides an additional method of forming a cellulosic substrate having a reduced absorbent capacity and capable of wicking liquid. A cellulosic substrate is provided having an inside and an outside. A hydrophobic treatment material is applied to the inside of the substrate in a continuous manner to reduce the absorbent capacity of the inside of the substrate. Wicking windows are formed between the outside and the inside that allow the passage of liquid. The wicking windows comprise cellulosic fibers from the outside of the substrate that are capable of wicking liquid contacting the inside of the substrate to the outside of the substrate.

An additional aspect of the present invention provides a method of forming a fabric having a reduced absorbent capacity and capable of wicking liquid. A first yarn is provided that comprises cellulosic fibers and has a reduced absorbent capacity. At least a portion of the cellulosic fibers are treated with a hydrophobic treatment comprising application of a material selected from the group consisting of silicones, fluorochemicals, zirconium compounds, oils, latexes, waxes, crosslinking resins, and blends thereof. A second yarn is provided that comprises cellulosic fibers and has a higher absorbent capacity than the first yarn. The first and second yarns are used to form a fabric that has an inside surface and an outside surface. The fabric is formed such that the inside surface has a lower absorbent capacity than the outside surface and such that the resulting fabric is capable of wicking liquid from the inside surface of the fabric to the outside surface of the fabric.

Yet a further aspect of the present invention provides a method of forming a nonwoven fabric having a reduced absorbent capacity and capable of wicking liquid. Cellulosic fibers are provided that are treated with a hydrophobic treatment and have a reduced absorbent capacity. Cellulosic fibers not treated with a hydrophobic treatment are provided that have a higher absorbent capacity than the treated fibers. The treated and untreated cellulosic fibers are used to form a nonwoven fabric that has an inside surface and an outside surface. The fabric is formed such that the inside surface has a reduced absorbent capacity and such that the resulting fabric is capable of wicking liquid from the inside surface of the fabric to the outside surface of the fabric. The fabric is formed by carding, air lay, wet lay, hydroentangling, thermal bonding, chemical bonding, needle punching, or combinations thereof.

Yet another aspect of the present invention provides a method of processing raw cotton fibers. Raw cotton fibers are provided that have natural hydrophobic waxes, natural hydrophobic oils, or combinations thereof. The raw cotton fibers are scoured with a base. The cotton fibers are also bleached with an oxidizing agent. The scouring and the bleaching are performed such that all or a portion of the natural waxes, natural oils, or combinations thereof are maintained on the resulting cotton fibers.

DETAILED DESCRIPTION OF THE INVENTION

Figure 1:
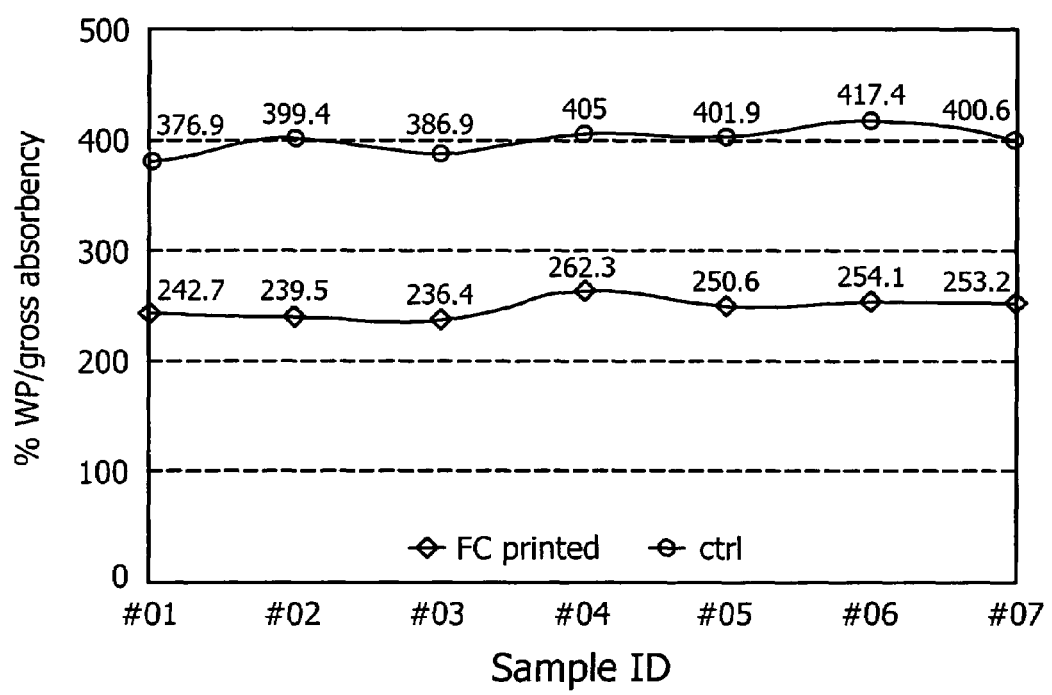
FIG. 1 is a graph showing the percent wet pickup of water (wt. percent/gross absorbency) for various treated samples in Example 1.

The present invention relates to cellulosic substrates with reduced absorbent capacity having the capability to wick liquids, as well as to methods of manufacturing such cellulosic substrates. The invention also relates to methods for reducing the absorbent capacity of cellulosic fibers, yarns, fabrics, garments, and other articles having cellulosic fibers.

According to the present invention, cellulosic fibers such as cotton may be used in products such as, for example, recreational performance apparel and topsheets of diapers and sanitary napkins, to provide the many comfort properties of such fibers without the disadvantage of the high absorbent capacity and moisture management problems of such fibers. In such embodiments, the cellulosic substrate (e.g., garment or absorbent product) is capable of wicking liquid (e.g., perspiration, urine, menstrual fluid) away from an inside of the substrate to an outside of the substrate where it can evaporate (e.g., when the substrate is a garment) or where it can be stored away from a wearer's body (e.g., when the substrate is an absorbent product such as a diaper).

Definitions

The following definitions are used herein:

The term "absorbent products" includes products such as, for example, towels, wipes, "cotton" balls, tampons, sanitary napkins, adult and baby diapers, medical and dental products including dental swabs, as well as other items. Absorbent products or components thereof may be formed from materials such as woven fabrics, knit fabrics, nonwoven fabrics, and the like.

The term "cellulosic substrate" as used herein refers to substrates that include cellulosic fibers such as cotton, jute, flax, hemp, ramie, lyocell, regenerated unsubstituted wood celluloses such as rayon, blends thereof, and blends with other fibrous materials (such as, for example, synthetic fibers) in which at least about 25 percent, preferably at least about 40 percent of the fibers are cellulosic materials. The cellulosic fibers preferably comprise cotton fibers. The cellulosic substrate may include non-cellulosic fibers (such as synthetic fibers and non-cellulosic natural fibers) including, for example, a polyolefin such as polypropylene or polyethylene, polyester, nylon, polyvinyl, polyurethane, acetate, mineral fibers, silk, wool, polylactic acid (PLA), or polytrimethyl terephthalate (PTT), and may include mixtures thereof. In addition, the cellulosic substrate may consist entirely of cellulosic fibers such as cotton. The substrate may be any article that contains cellulosic fibers in the requisite amount, and includes, for example, woven fabrics, knit fabrics, nonwoven fabrics, multilayer fabrics, garments, yarns, absorbent products, topsheets of absorbent products, and the like. The cellulosic substrates of the present invention include substrates having an "inside" and an "outside." The "inside" of such cellulosic substrates comprises at least an inside surface of the substrate and may include all or a portion of the interior of the substrate. The "outside" of such cellulosic substrates comprises at least an outside surface of the substrate and may include all or a portion of the interior of the substrate. Generally, the inside surface of such cellulosic substrates contacts a user's skin while in use.

The term "fabric" includes woven fabrics, knit fabrics, nonwoven fabrics, multilayer fabrics, and the like.

The terms "gross absorbency" and "absorbent capacity" are used interchangeably herein to mean the mass of liquid (e.g., perspiration, water, urine, menstrual fluid, etc.) which is picked up or contained in a fiber, fabric, garment, or other substrate which is exposed to the liquid under conditions of use. In other words, the absorbent capacity is the total amount of liquid moisture which a fiber, fabric, garment, or other substrate will pick up or hold when in contact with excess liquid moisture from a wet surface such as skin. More specifically, absorbent capacity is the mass of liquid per unit mass of fiber, fabric, garment, or other substrate at saturation.

The term "reduced absorbent capacity" as used herein means that the absorbent capacity of the fiber, fabric, cellulosic substrate, or other article is lower than the normal, standard, or regular absorbent capacity of the fiber, fabric, cellulosic substrate, or other article. The term "reduced absorbent capacity" describes fiber, fabric, cellulosic substrates, or other articles whose absorbent capacity has been reduced or lowered by methods described herein to below the normal, standard, or regular absorbent capacity of the fiber, fabric, cellulosic substrate, or other article. The term "reduced absorbent capacity" also describes fiber such as cotton that has been subjected to a modified scouring and bleaching process as described herein such that the fiber has a lower absorbent capacity than fiber subjected to a normal scouring and bleaching process.

According to the present invention, the absorbent capacity of the fabric, garment, or other cellulosic substrate is reduced. There are a variety of commercially available chemical treatments and yarn and fabric construction options to reduce the absorbent capacity of hydrophilic cellulosic fibers or cellulosic materials such as cotton. In addition, the normal preparation process of hydrophilic cellulosic fibers may be modified to produce fibers with reduced absorbent capacity. A possible consideration when choosing a chemical treatment, modified preparation process or construction option from the large number of options is the durability of the option to home laundering and tumble drying.

One method to reduce the absorbent capacity of a garment is to use a thin fabric to make the garment. This is a major factor for the acceptable performance of many synthetic performance garments. With other factors held constant, the thinner the fabric, the less internal void capillary spaces to absorb and hold liquid. A related method to reduce the absorbent capacity of a garment is to use finer yarns, which allow thinner fabrics to be made. The yarns may be tightly twisted to further minimize capillary void volume within the structure of the individual yarn. Further, the fabric may be made in tight construction while maintaining an overall thin fabric.

Another option for preparing garments for use in certain activities and environments is to make thin but open fabric structures such as warp knits. Eyelet fabrics can be made by those of skill in the art which are open, thin, and light weight, but which are made from yarns which have sufficient twist to minimize the capillary spaces inside the yarns. Water or perspiration held in the fine capillary spaces between fibers in the yarn is held tightly and therefore more difficult to release. For example, in more extreme situations of complete saturation of the garment, perspiration held in the relatively large capillaries which are the holes in an eyelet warp knit fabric can be readily removed by shaking the fabric. This loosely held water may even be released from a fully saturated garment during the natural movement of the wearer's activity, such as the bouncing or jarring that occurs during running.

The absorbent capacity of a fiber, yarn, fabric, garment, or other cellulosic substrate can also be reduced by chemical treatments that are used to introduce hydrophobicity into the fiber, yarn, fabric, or other cellulosic substrate. The chemical treatments are referred to herein as "hydrophobic treatments" and include application of any material or materials (referred to herein as a "hydrophobic treatment chemical") that are capable of introducing hydrophobicity into a fiber, yarn, fabric, garment, or other substrate. Hydrophobic treatments of the present invention include application of a hydrophobic treatment material such as, for example, silicones, fluorochemicals, zirconium compounds, oils, latexes, waxes and a variety of others including crosslinking resins such as dimethylol dihydroxy ethylene urea (DMDHEU), urea formaldehyde, ethylene urea, melamine resins, dimethyl urea glyoxal (DMUG), carboxylic acids and polycarboxylic acids including citric, maleic, butane tetra carboxylic, polymaleic acids, and many others. Blends of these and other hydrophobic treatment materials may also be used. When manufacturing certain products such as, for example, recreational performance apparel, according to the present invention, it may be desirable to choose a treatment chemistry that is durable to multiple home launderings. In the case of disposable absorbent products, however, the choice of chemical treatments may be much broader because durability to home laundering is not needed. The chemical treatments may be done on fiber, yarn, fabric, or the completed cellulosic substrate (e.g., garment) or other article.

The normal preparation process (i.e., scouring and bleaching) of cellulosic fiber, such as cotton, that is used to purify the fiber, whiten the fiber, and make the fiber absorbent may also be modified to produce fiber with reduced absorbent capacity. In the normal scouring step of the preparation process, a base such as a sodium hydroxide solution is first applied to the fiber at an elevated temperature and pressure to saponify the natural oils and waxes of the raw fiber and soften impurities in the raw fiber so that they can be washed away. In the normal bleaching step of the preparation process, an oxidizing agent such as hydrogen peroxide or sodium hypochlorite is applied to the fiber at an elevated temperature and pressure to whiten and further purify the fiber. The conditions, equipment, and agents used to carry out the normal scouring and bleaching steps are known to those skilled in the art. According to the present invention, the modification of this normal preparation process involves reducing the concentration of one or both of the base or the oxidizing agent, replacing the base and/or the oxidizing agents with other agents, reducing the time of one or both of the scouring or bleaching steps, and/or reducing the temperature in one or both of the scouring or bleaching steps. By modifying the normal scouring and bleaching process, fiber may be produced that is at least partially purified and bleached without removing all of the natural waxes and/or oils on the fiber surface (i.e., all or a portion of the natural waxes and/or oils on the fiber surface are maintained), such that the resulting fiber has a reduced absorbent capacity as compared to normal scoured and bleached cotton. The modification of the present invention may be adjusted as needed to achieve the desired level of purification and whitening as well as the desired level of absorbency/hydrophobicity in the resulting fibers. The resulting fibers may be used in accordance with the present invention alone or may be blended with normal hydrophilic cotton (i.e., cotton that has been subjected to the normal scouring and bleaching process) or other natural or synthetic fibers. Although the modification of the normal scouring and bleaching process according to the present invention may leave some natural particulates in the resulting fiber, the impurities may be minimized if desired by beginning the process with cleaner raw cotton or by mechanically cleaning the cotton before or after the modified process.

In accordance with the present invention, cellulosic substrates with reduced absorbent capacity are provided that are capable of wicking liquid contacting an inside of the substrate to an outside of the substrate. Several methods may be used in order to achieve such a cellulosic substrate capable of wicking liquids. In one preferred aspect of the invention, a hydrophobic treatment is used, either by subjecting the completed cellulosic substrate to the hydrophobic treatment or subjecting the material used to construct the substrate (e.g., cellulosic fibers, yarns, etc.) to the hydrophobic treatment.

In some embodiments of the invention (as further described below), not all of the fiber, yarn, fabric, or other cellulosic substrate is made highly hydrophobic. In this aspect, the hydrophobicity of the inside of a cellulosic substrate is made to be discontinuous in order to allow liquid to be wicked from the inside to the outside of the substrate through fibers which have not been made hydrophobic through treatment (i.e., hydrophilic fibers) remaining on the inside of the substrate. The hydrophilic fibers on the inside of the substrate form channels that act as "wicking windows" to allow liquid to move from the inside of the substrate to the outside. In one method, a hydrophobic treatment material may be applied to a cellulosic substrate (e.g., fabric, garment, topsheet, etc.) in a discontinuous manner such that (1) the absorbent capacity of the inside of the substrate is reduced to below the absorbent capacity of the outside of the substrate and (2) the substrate is capable of wicking liquid contacting the inside of the substrate to the outside of the substrate. In another method, a hydrophobic treatment material is applied to a portion of the cellulosic fibers used to form the inside of the cellulosic substrate. For example, a hydrophobic treatment material could be applied to a portion of the fibers used to form a nonwoven topsheet of a diaper or sanitary napkin. In yet another method, the inside of a cellulosic substrate is formed from a yarn comprising a blend of cellulosic fibers treated with a hydrophobic treatment and cellulosic fibers not treated with a hydrophobic treatment. In a further method, the inside of a cellulosic substrate is formed from at least two yarns where a first yarn is treated with a hydrophobic treatment and a second yarn is not treated with a hydrophobic treatment.

In other embodiments of the invention (as further described below), the entire inside of a cellulosic substrate is made to be hydrophobic. The cellulosic substrate could be subjected to a continuous hydrophobic treatment, or a hydrophobic treatment material could be applied to the fibers, yarn, or fabric used to form the cellulosic substrate. Using methods described in more detail below, channels or "wicking windows" are formed between an inside of the substrate and an outside of the substrate that allow liquid to be wicked from the inside to the outside. For example, wicking windows can be formed in a cellulosic substrate that includes an inside treated with a continuous hydrophobic treatment and an outside having hydrophilic fibers by using needle punching or hydroentangling techniques. Techniques such as needle punching push hydrophilic cellulosic fibers from the outside of the substrate through the inside to serve as pathways for wicking liquid from the inside to the outside of the substrate.

A range of performance characteristics can be built into a cellulosic substrate by controlling the amount of treated versus untreated fibers or yarns which are used to make the substrate, or, alternatively, by treating only controlled portions of the completed substrate. These techniques then allow substrates to be engineered for specific activities, levels of activities, or combinations of activities and environmental conditions, as well as personal preferences of the wearer or user of the substrate.

One means of controlling the amount or ratio of the treated versus untreated fiber (i.e., the hydrophobic/reduced absorbency fiber versus the hydrophilic fiber) in a substrate is to perform the treatment of the hydrophilic fiber (e.g. cotton, rayon, etc.) on the fiber itself before conversion into yarn, fabric, or other cellulosic substrate. Both the level of treatment and the blend ratio of treated versus untreated fiber can be controlled. If desired, yarn may be spun from 100% treated fiber and a similar or different yarn may be spun from untreated fiber. The ratio of treated versus untreated fiber may be varied from 100/0 to 0/100 within any given yarn. Yarns with different ratios of treated versus untreated fibers may then be used to construct a woven or knit fabric.

The woven, knit and nonwoven fabrics of the present invention can be any area density that is practical from a manufacturing standpoint. However, fabrics with lower area densities can be beneficial in some embodiments, as they tend to lower the gross absorbency of the resulting garments or other articles of manufacture.

The fibers, yarns, and other materials with reduced absorbent capacity according to the present invention can be used for many purposes, including articles of recreational performance apparel and absorbent products such as diapers and sanitary napkins. Raincoats, awnings, yarn, fibers and fabrics, each with a reduced gross absorption as compared with similar, but untreated materials, are also within the scope of the invention.

The following embodiments are described in connection with applications involving garments and absorbent products. However, the techniques, yarns, and fabrics described in the embodiments may also be applied to any other cellulosic substrate or article of manufacture.

Embodiments Related to Garments

Embodiment 1

Embodiment 1 involves using blends of raw cotton and treated cotton fiber. A knit, woven, nonwoven fabric, or multilayered fabric using combinations thereof, can be made from two or more yarns (or ends). Those skilled in the art of knitting or weaving can place one yarn (Yarn A) in the fabric primarily on the inside of the fabric (the side to be worn next to the skin). Yarn A may contain a certain ratio by weight of treated and untreated fibers, for example, 70/30 by weight treated (reduced absorbent capacity) cotton (or other cellulosic) fiber and untreated (normal or natural absorbent capacity) cotton (or other cellulosic) fiber. A garment made from this yarn (which is the predominant yarn next to the skin) will have much reduced hydrophilic properties, and the inside of the garment will also have much reduced hydrophilic properties. Therefore, Yarn A (and the inside of the garment), having less affinity for water (or perspiration) will have a much reduced tendency to stick to the skin during times or activities where perspiration (liquid) begins to form or later in the activity cycle if the garment becomes saturated. The reduced tendency to stick to the skin will increase the freedom of movement, or at least the perception of freedom of movement. Therefore, the potential performance and/or the perception of comfort of the wearer is improved. The untreated portion of the fiber in Yarn A maintains excellent wicking properties and will pull (liquid) perspiration away from the skin. The garment will also dry faster because it will have reduced absorbent capacity.

A second (or third) yarn (Yarn B) may be used to make this same woven or knit fabric. Using techniques known by those skilled in the art of knitting or weaving, Yarn B may be placed predominantly on the outside of the fabric (that is the side to be worn on the outside of the garment). Yarn B may also contain a ratio of treated to untreated fibers, for example, a ratio of 30/70 by weight treated (reduced absorbent capacity) to untreated fiber, respectively. Since Yarn B is primarily untreated and highly absorbent (on the outside of the garment) it will tend to wick (liquid) moisture away from Yarn A on the inside of the garment. This mass transfer of perspiration away from the interface of the inside of the garment and the skin will tend to keep the individual dryer, enhancing the perception of comfort. Since Yarn B is the predominant yarn on the outside of the garment and is mostly hydrophilic, the outer surface of the garment will become wet if the wearer continues to perspire at a sufficient rate. The liquid moisture in this example is free to spread (wick) over the majority of the outside of the garment. The pulling of the moisture from the skin and transporting to the outside of the garment, where the moisture spreads (by natural capillary movement or wicking) over the outside of the garment, aids in the perception of comfort. With the moisture spreading on the outside of the garment, it is important to increase the surface area which is wet. The more wetted surface area on the outside of the garment, the more rapid the overall evaporation rate (i.e. mass of water evaporated per unit time) since the evaporation rate is dependent on the surface area exposed to the outside environment (in most situations, assuming the outside environment is not at 100% relative humidity). The outside of the garment can be made of completely untreated fiber or yarn to maximize wicking away from the skin and surface area for evaporative cooling.

Any of the yarns that are used in this method, which are made from blends of treated and untreated cotton, may be intimate blends or mechanical blends. Intimate blends are made by mixing the fiber, usually at the opening hoppers. In mechanical blends, the two fibers are blended in a downstream process such as during drawing. These alternatives further add options for the engineering of fabric and garments for specific end use activities, environmental conditions, or personal preferences.

Another option is to begin with one or more yarns in a fabric that includes a blend of raw cotton and scoured cotton (or scoured and bleached cotton); or scoured cotton which has been dyed (stock dyed). Here, the blends of these two cottons can be used at the ratios stated above or at any ratio desired by the fabric or garment designer. The objective is to achieve reduced absorbent capacity in the fabric, while maintaining the natural wicking, breathability, moisture regain, moisture vapor transport, softness and the other desirable properties of cotton for use in clothing. In this case, the hydrophobic chemical treatments may be done on fabric using any of the normal equipment and processing routes for fabric. However, it is preferred that no scouring, washing or excessive wet processing is done to the fabric prior to application of the hydrophobic treatment to the fabric. Such wet processing may tend to remove the natural oils and waxes which coat the raw cotton fiber in the blend. The natural oils and waxes on the raw cotton can serve as a "resist" treatment. When the hydrophobic treatment is applied to the fabric it will preferentially deposit on the absorbent scoured or scoured and bleached (or dyed) fiber in the yarn. After application of the hydrophobic treatment, the fabric is then preferably subjected to a drying and curing process specific for fixing or curing the specific treatment.

As an example, a crosslinkable hydrophobic water and oil repellent fluorochemical such as Repearl F-35 (concentrated fluorochemical water and oil repellent finish) may be applied to the fabric with the recommended crosslinking agent, Repearl MF (a blocked isocyanate reactive cross-linking finishing agent). The treated fabric may be dried at about 110° C. for 1 to 3 minutes and then cured at 160° C. for 2 minutes. Any of the Repearl F-35 and MF which may deposit on the raw cotton portion of the blend of raw cotton and scoured, bleached or dyed cotton, will be blocked from cross-linking with the raw cotton by the layer of natural cotton oils and waxes which are present on the cotton fiber. The Repearl products can be removed from the raw cotton portion of the blend in a subsequent scouring operation. In this example, a variety of dye shades can be produced by starting with stock dyed cotton rather than scoured only or scoured and bleached cotton, to be blended with the raw cotton. Since the outside of the garment is predominately made from such dyed fiber rather than raw cotton, dark shades will be possible. Another option is to dye the fabric, since the side to be worn on the outside of the garment will be predominantly regular hydrophilic (absorbent) cotton which will take dyes. Optionally, in place of the scoured or scoured and bleached cotton, raw cotton or scoured or scoured and bleached cotton with a resist treatment may be used.

Advantages: The treated garment maintains the benefits of evaporative cooling because the liquid moisture is free to spread on the outside of the garment, where the amount of wetted surface area on the outside of the garment will be a major influence on evaporation rate. Second, the garment will have less tendency to stick to the skin and restrict movement. Third, the overall absorbent capacity of the garment is much reduced in comparison to 100% untreated cotton by including cotton (and/or other hydrophilic fibers) which has been treated to reduce its absorbent capacity. This reduction in overall absorbent capacity of the garment means that the garment will not become as heavy as a 100% untreated cotton garment as the garment becomes saturated. The reduced weight of the (wet) garment translates into improved performance of the wearer or at least the perception of improved performance as well as a further improvement in the perception of comfort. Fourth, the reduced absorbent capacity of the garment translates into less sagging of the garment. Fifth, the garment will dry faster than 100% untreated cotton. The time required for a wet garment to dry depends on the amount of liquid contained in the garment. As the garment reaches saturation, this amount of liquid is equal to the absorbent capacity of the garment. If the wearer leaves on the wet garment described in this example after exercise or activity, there will be less tendency for the individual to become chilled relative to a pure untreated cotton garment. After exercise or completion of whatever activity cause the perspiration, the body temperature begins to drop back to the resting temperature and because the garment contains less moisture, there will be less evaporative cooling. The layer of fiber or yarn which is next to the skin is primarily treated so that it has much reduced absorbent capacity and stays relatively dry. This relatively dry layer next to the skin further reduces the discomfort of a cold wet fabric next to the skin, when the wearer may become chilled if the outside (or indoor) environment is cool or cold. The relatively dry layer of fiber or yarn next to the skin serves to insulate the skin from the relatively wet and potentially cold outside of the garment. That is, the transfer of body heat through the relatively dry layer (inside layer) which is next to the skin is reduced in comparison to the heat transfer through a wet fabric. If the garment is taken off and allowed to air dry or machine dry, it will dry faster and with less energy.

Examples of treatments for reducing the absorbent capacity of hydrophilic fibers, yarns, fabrics or garment include application of fluorocarbons (e.g., Teflon® brand, Repearl® brand, Nuva® brand, etc.) that do not adversely affect cotton's beneficial properties, for example, the comfort properties during "normal" wearing when the wearer and the garment are in the dry state without significant perspiration. Fluorocarbon treatments can make cotton very hydrophobic. Such treatments can be used in the above example or in the practice of this invention in general. These treatments (e.g., fluorocarbons and silicones) can be applied to cotton without reducing the natural moisture regain, natural moisture vapor transport or the natural breathability of cotton fabrics and garments. Therefore, when performance garments are made as described in these examples, the basic comfort properties of cotton that are present during "normal" (dry) wearing of regular (untreated) cotton garments will also be present in garments containing treated fiber, yarn or fabric.

Synthetic fibers such as polyester and polypropylene have very low moisture regains. Moisture vapor is given off by the body of an average human subject at rest at a rate of about ¼ cup per hour. The rate of moisture vapor given off by the body can increase substantially as the rate of activity increases. On synthetic fibers which are inherently hydrophobic (such as polyester and polypropylene), this moisture vapor can quickly condense on the fibers as liquid water and make the garment feel clammy which can have a significant negative impact on the perception of comfort by the wearer. However, even cotton which has been completely treated (e.g. in fabric form by padding) with fluorocarbons has been found to maintain the normal moisture regain of untreated (regular) cotton which is about 7.5% under standard conditions. As the relative humidity increases in the microclimate between the garment and the skin, and in the thin boundary layer of air on the outside of the garment, the moisture regain of cotton increases for both treated (using treatments which make the cotton hydrophobic such as fluorocarbon) and untreated cotton. Hence the cotton can adsorb more moisture from this microclimate before any liquid moisture is present. This means that even for treated cotton, or the blends of treated and untreated cotton, cited in these examples, the onset of the presence of liquid moisture will occur later in the exercise or activity cycle. Therefore, the perception of staying dry (and not clammy) is maintained for a longer period of time, which translates into increased comfort.

Hydrophobic treatments such as application of fluorocarbons, silicones, and waxes are generally thought to function by forming a film on the outside of the fibers. At normal application levels this film is highly discontinuous, to the extent of being closer to microscopic "globs" of polymer or wax on the surface of the hydrophilic fibers. The treatments do produce hydrophobic fibers, fabrics and yarns from those which were previously hydrophilic because the surface tension of water or perspiration generally does not allow the penetration of liquid into the fibers and reduces wicking in the capillaries formed between treated fibers or yarns.

A further advantage of using blends of treated and untreated fiber (such as cotton) to make yarns for recreational performance apparel is that the uniformity of treatment is not critical since the blending operation prior to yarn making, will tend to "even out" any nonuniformity in the treatment chemistry. It will be possible to make heathers by dyeing yarn, fabric or garments made from blends of treated and untreated fiber. If solid shades are desired, then it may be necessary to stock dye prior to the finishing treatments to make a portion of the fiber hydrophobic as described above. Dyeing is preferably done prior to such finishing treatments regardless of whether the treatments are done on fiber, fabric, yarn or garments. It is noted that in embodiments where the outside of the fabric or garment is completely untreated, there will be little or no impact on the dyed appearance of the outside of the fabric or garment.

In this embodiment, the ratio of treated fiber to untreated fiber in Yarn A may range from 99/1 to 10/90. The preferred ratio is from about 90/10 to about 20/80.

Embodiment 2

Embodiment 2 involves using yarn treatments. Equipment to treat fiber is not as widely available as equipment that is used to treat yarn. When fiber such as cotton is wet processed the spinnability must be considered and often a spin finish must be added. In embodiment 1, since each of the yarns contains some untreated cotton fiber, the untreated cotton can serve as a "carrier" for the treated cotton and therefore reduce the demands on a spin finish or in some cases it may eliminate the need for a spin finish. Another option is to treat yarn.

In this embodiment, a 100% cotton (or other cellulosic fiber) fabric is made from two (2) or more yarns. Yarn A can be treated to increase its hydrophobicity using the same chemistry described in embodiment 1. Yarn B is untreated cotton (and/or another cellulosic material or a blend thereof, optionally with a non-cellulosic material). Those skilled in the art of knitting or weaving can make fabrics which include Yarn A predominantly on the inside of the garment and Yarn B predominantly on the outside of the garment. The fabric can be made in such a way that the highly absorbent yarn B may vary as a fraction of the surface area of the inside of the fabric or garment. For example, the inside surface of the garment may be 70% treated Yarn A and 30% untreated Yarn B. The advantages listed above in embodiment 1 also apply to embodiment 2.

Making the new class of recreational performance apparel from 100% cotton or other yarns using a blend of treated and untreated yarn rather than a blend of treated and untreated fiber provides somewhat less versatility for the designer. Our laboratory work has shown that varying the level of treatment typically will affect the hydrophobicity of the treated substrate (fiber, yarn fabric, or garment) only to a limited extent. The level of treatment can have a major influence on the durability of the treatments to operations such as home laundering. Choosing hydrophobic treatments such as Repearl®F35 combined with crosslinking compound Repearl® MF brand (Mitsubishi Chemical) fluorochemicals can allow treatments which are durable to many home launderings. Treatments are available which permanently crosslink to cotton and other cellulosic materials.

Optionally, resist treatments can be applied on a portion of the yarn that will form the garment. A resist is a substance that will prevent a subsequent treatment (e.g., a hydrophobic treatment to reduce absorbent capacity) from penetrating or forming a permanent bond with the substrate or portion of the substrate to which it was applied.

For example, a recreational performance garment may be made from two or more yarns, including Yarn A and Yarn B. Yarn A and Yarn B can both be made from 100% cotton and/or other hydrophilic fiber. Yarn A and B can both be scoured, bleached, and dyed to the same shade or completely different colors. At the end of the respective dye cycles for each of the yarns, a resist treatment can be given to Yarn B but not to Yarn A prior to drying the yarns. The resist treatment can include a variety of treatments known to those who are skilled in the art of resist printing. For example, treatments may be used which are appropriate to prevent a fluorocarbon or other durable water repellent treatment (i.e. hydrophobic treatment) from bonding to the surface of the fibers which include Yarn B. A woven or knit fabric can be made from Yarn A and Yarn B. Other yarns can be included if desired but for the purpose of this example, the fabric will be made only from Yarn A and B. Those skilled in the art of weaving or knitting can place the yarns in the woven or knit fabric in such a way that Yarn B is predominantly on the face of the fabric which is the side to be made into the outside of the garment. The ratio of the surface area on the outside of the garment which has Yarn B exposed, relative to the surface area which has Yarn A exposed, can be engineered by the weaver or knitter over a broad range. The ratio of Yarn B to Yarn A on the outside of the garment may range from 99/1 to 10/90. A preferred range is 95/1 to 30/70. After the fabric is made containing the two yarns it can be finished in piece form with the durable hydrophobic treatments such as application of fluorochemicals, silicones, or waxes, etc. Appropriate crosslinking agents can be included in the formula to ensure good durability to the preferred cleaning procedure, which is typically home laundering. Since Yarn B is predominantly on the outside of the fabric and includes the resist treatment, the hydrophobic treatment material will be preferentially deposited on the more absorbent and receptive Yarn A, which does not contain the resist. The resist can be designed in such a way to be readily removed by a scouring process, for example, water with a detergent or a mild alkaline solution. If the resist is formulated and/or applied in such a way that the durable hydrophobic treatment material deposits on the yarn containing the resist, it cannot bond to the cotton fiber (which contains the resist). Consequently, any of the durable hydrophobic treatment (e.g. fluorocarbon or silicone) which deposits on Yarn A containing the resist can be readily removed in a subsequent wash or scour. The subsequent wash or scour can be done at the mill or by the consumer in the home laundry.

The technique described here (i.e. using a resist) eliminates potential difficulties with yarn application of durable hydrophobic treatments, such as filtering by the yarn package or breaking of the emulsion by the shear forces in the package machine.

Another possibility for yarn treatments is to apply the hydrophobic treatments directly to the yarn in a discontinuous manner, such as by space dyeing or sprays. The same logic applies here as in the fiber treatment or above yarn treatment examples. Such yarn can be used to produce garments with reduced absorbent capacity while maintaining the necessary degree of wicking for the activity and environment.

Embodiment 3

Embodiment 3 involves fabric treatments which are performed in a discontinuous fashion rather than typical commercial treatments which are done in a continuous fashion (meaning that they result in a continuous application of the hydrophobic treatment to the fabric). In this embodiment, the treatment must result in a discontinuous finish. The discontinuous nature of the finishing treatment in the end product or garment is a key feature in the above embodiments as well. If a highly hydrophobic finishing treatment is applied in a continuous fashion on a hydrophilic fabric such as cotton, the garment will not wick. If the garment does not wick, moisture will not be transported away from the skin. The garment will tend to stay dry even when the wearer is perspiring heavily, but the liquid will predominantly run or drip down the body because it can not readily pass into the garment (in the Z direction—meaning normal to the plane of the fabric). Also the microclimate between the skin and the garment will quickly approach 100% relative humidity and the result is a very uncomfortable garment.

Figure 4:
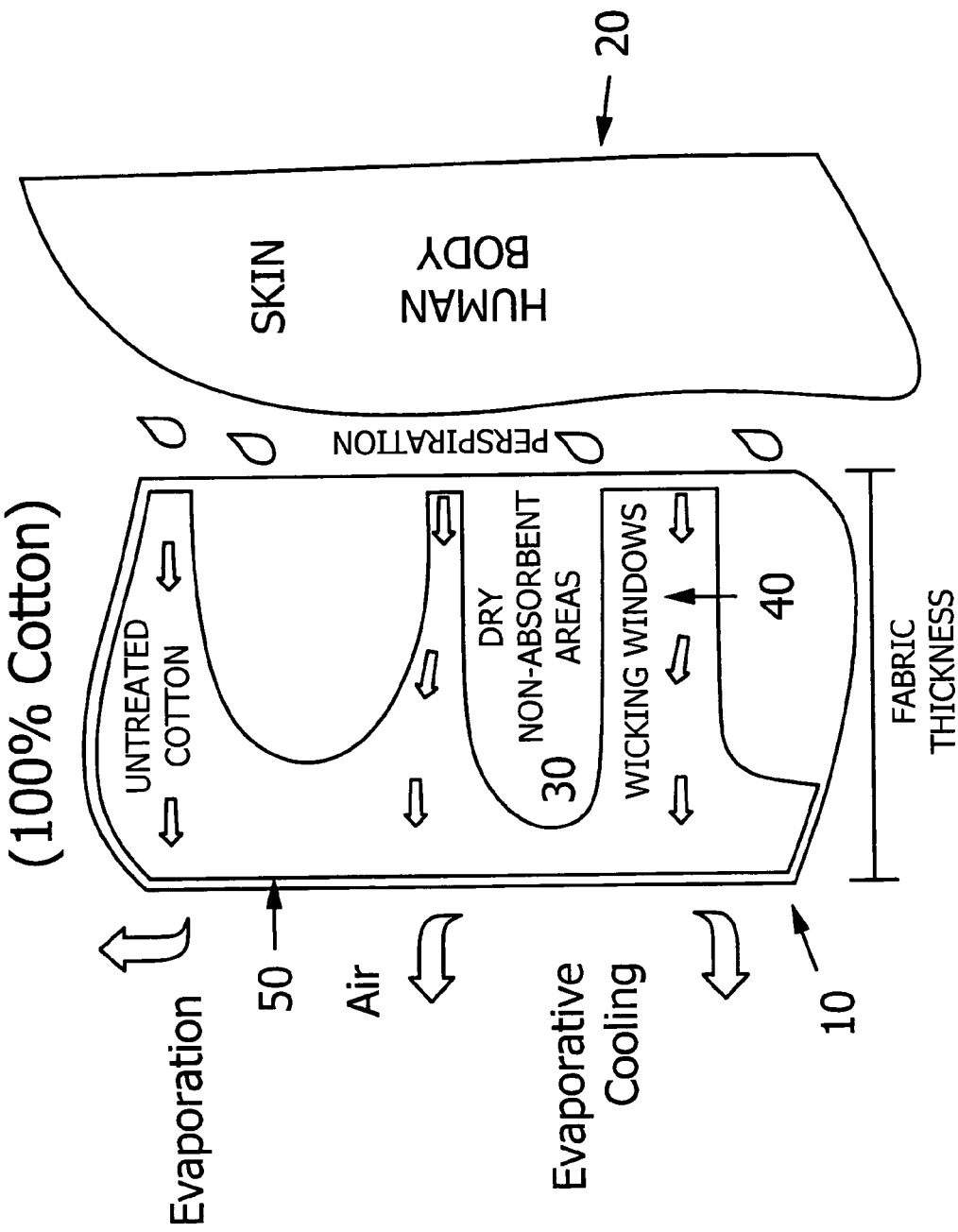
FIG. 4 is an illustration of a treated fabric placed against the skin of the wearer showing the path through which perspiration passes through the inside of the fabric to the outer layer of the fabric.

An example of the treated fabric is shown in FIG. 4. A treated fabric (10) is placed against the skin of the wearer (20) and perspiration is generated through the activity of the wearer. The perspiration does not pass through the non-absorbent areas (30) but does pass through the wicking windows (40) to the outer layer of the fabric (50) where it can evaporate, resulting in evaporative cooling.

On fabric, the discontinuous treatments may be done, for example, by printing, dripping, foam or spraying. Resist treatments may be used on the fabric in a similar discontinuous manner. Suitable resist treatments include any treatment that can be applied to the fabric that will block the hydrophobic treatments from forming a permanent bond with the fibers, yarns or fabric. Resist treatments can be removed by a subsequent washing, scouring or rinsing operation and will allow any hydrophobic treatments which were applied on top of the areas that were resist treated to also be removed or washed away from those areas. There are a wide variety of resist treatments that can be used, and anything that prevents a subsequent hydrophobic treatment from bonding in that area may be suitable. Examples of such resist treatments include natural and synthetic gums and resins, emulsifiable oils or waxes and a variety of natural or synthetic polymers. Resist treatments require at least two steps. First, the resist treatment is applied, with or without an intermediate drying step. Second, the hydrophobic treatment can be applied directly to the fabric. The application can be accomplished by any common application technique that is normally used for applying dyes and finishes to fabrics. These include, for example, padding, dipping, sprays, foams, weirs, and the like, and may include the subsequent extraction of the excess liquor by squeezing, vacuum, doctor blades, air knives, centrifuges, etc.

Direct application of the hydrophobic treatment is another option, but the treatments must be applied in a discontinuous manner. In both the resist method described above and the direct application method, the ratio of treated surface area to untreated surface area on both the inside and outside of the fabric is an important consideration. The size and design of the areas or islands to be treated versus those to be left untreated are also important. These many design options allow for substantial versatility and creativity by the designer of this apparel. As in embodiment 1 (above), garments can be made from 100% cotton and can be tailored to the specific activity, environment and personal preferences of the wearer.

Printing fabric with dyes or pigments is a common method of coloration. There are several printing techniques that can be used, including gravure, roller and screen printing. Any of the commercially practiced printing techniques can be used in this embodiment. The printing may be done with or without colorants. Any of the durable hydrophobic treating agents as described above, such as fluorochemicals, silicones, waxes or other materials, may be used. If dying to a solid shade is to be done, it is preferably done before printing with the above-mentioned treating agents.

Those skilled in the art of printing are familiar with various thickeners which are used to keep the colorants in the normal printing process from migrating and to maintain a clear or well-defined print. In printing in general, there are a number of variables which can be controlled. Some variables such as print paste viscosity, amount of print paste applied, roller/wiper pressure, speed, etc., can be used to control the depth of penetration of the print paste.

One option is to print on the face of the fabric (the side to be worn outside) and adjust the variables mentioned above (such as print paste viscosity) to allow the print paste containing the hydrophobic treatment (with or without colorant) to pass through to the back of the fabric (the side to be worn on the inside of the garment). A garment can be made where 50% of the fabric from which the garment is made is printed with the print paste containing the hydrophobic agent or chemical(s). Penetration of the print paste may be complete from the face to the back of the fabric. The print pattern may be simple or complex and the size of the pattern may vary. The pattern may be, for example, stripes or dots but the size is preferably relatively small to distribute the untreated fiber which can serve as the wicking medium, uniformly throughout the fabric and garment.

In one embodiment, the print pattern includes circles (dots) ranging from 1 mm to 50 mm in diameter, with spacing between the dots equal to the diameter of the dot. A preferred range for the diameter of the dots and spacing between the dots (in both X and Y directions) is 2 mm to 20 mm. A more preferred spacing is 2 mm to 10 mm. The spacing of the print pattern does not need to be uniform and the pattern itself may vary over an almost infinite range.

A "wicking window" effect may also be achieved with this technique. By "wicking window" we mean untreated areas in the garment, due to a print pattern which allows liquid moisture (or perspiration) to pass through from the inside of the garment to the outside of the garment. Performance characteristics of the garment, using the printing method of manufacture, may be further enhanced by printing on the back of the fabric (the side to be worn next to the skin) rather than the face. The print paste viscosity and other printing variables can be controlled to limit the depth of penetration of the print paste (containing the hydrophobic treatment) into the fabric in the Z direction. These printing variables can be adjusted such that the print paste and the subsequent hydrophobic islands do not penetrate to the face of the fabric. A garment can be produced using these techniques which is predominantly hydrophobic on the inside and predominantly hydrophilic on the outside. By having many small areas (i.e., a small print pattern) on the inside of the garment which are untreated and highly wicking, liquid moisture will be pulled away from the body through these "wicking windows" and into the outside of the garment, which is predominantly untreated and highly wickable. In this example, the outside of the fabric from which the garments are made may be completely untreated so that maximum evaporation rate and evaporative cooling can be maintained, if desired. The inside of the garment, which overall is more hydrophobic, will have a much reduced absorbent capacity and a much reduced tendency to stick to the (hydrophilic) skin of the wearer. This embodiment allows for creativity in the design of such garments. Garments made by this technique can be engineered to the activity, environment and or the preferences of the wearer.

Optionally, designs, letters, words, symbols, characters or other two dimensional shapes can be printed into the fabric (or knit or woven into the fabric, by using combinations of treated and untreated yarns). This can be accomplished, for example, by adding a colorant to the print paste, which also includes the durable hydrophobic treatment chemistry(ies). It is generally known that wet fabric or garments have a different appearance in many cases and for many colors, than dry fabric or garments. In this embodiment, the print pattern may be microscopic in size or at least so small that it is not plainly visible. Performance apparel can be created using larger designs which are highly visible and still maintain most if not all of the advantages listed above in embodiment 1.

The printing technique described in this embodiment may be performed on bleached goods or on dyed goods. For most shades, with the exception of very dark shades, wet areas of a fabric or garment have a darker appearance than dry areas. Consequently, if the print pattern is printed onto the outside of the fabric (the side to be worn outside) the hydrophobic treatment will keep the printed area from becoming wet during exercise, or activities involving perspiration, or when worn outdoors under conditions of precipitation. Hence, the print pattern will be visible, but only (or predominantly) when the garment becomes wet. This effect can also be achieved when printing on the inside of the fabric, if the printing variables such as print paste viscosity are adjusted to allow the print paste to penetrate to the outside of the fabric. Accordingly, designs, letters, words, symbols, characters or other two dimensional shapes can be printed onto the fabric (or garment) that will become visible when the garment becomes wet. This concept can be used in conjunction with recreational performance apparel or on other products including non apparel items that may be used in the shower or bath by children or others, swimwear, umbrellas, raincoats etc. In some cases, other than recreational performance apparel, it may be desirable to have a two sided treatment, such as for raincoats or umbrellas. The inside of the product may be fully treated with a durable water repellant, such as the inside of a raincoat or umbrella. The outside may be printed (or the design created by knitting or weaving) in a pattern desired by the consumer. Two layered fabrics or laminates of two or more layers may also be used to create the desired effect. This can allow for a design or logo to appear when the product becomes wet. This effect may be most pronounced when there is no dye or pigment used in the print paste containing the hydrophobic treatment.

Embodiment 4

Embodiment 4 involves forming multilayer fabrics. The fabrics in this embodiment may incorporate wovens, knits, or nonwovens or combinations thereof. In the case of nonwovens, the layers may be very thin so that such multi-layered fabrics are not necessarily very heavy. Such fabrics may be used as single layers or as one of the layers in a layered system of dress for a particular activity, such as backpacking or snow skiing.

In one embodiment, two layers are used. One layer, Layer A, is a hydrophilic fiber fabric (such as cotton) that has been treated to render it hydrophobic with much reduced absorbent capacity under normal conditions of use. A second layer, Layer B, is an untreated hydrophilic fabric such as cotton. The hydrophilic Layer B may be used as the outside layer to produce a performance garment for activities involving perspiration. The two layers may be attached using methods well known to those of skill in the art, including laminating using heat and pressure with various bonding agents such as (low melting) thermoplastic powders, fibers or films. If films are used, they are preferably breathable. Other types of chemical bonding can also be used and may be applied by coating or any one sided application technique such as foam, spray, doctor blade, etc. Strictly mechanical means of bonding the layers can also be used, for example, needle punching, stitch-bonding, or hydroentangling (also known as spunlace or water jet entangling).

To produce wicking or capillary movement of liquid (i.e., perspiration) from the inside of the garment to the outside of the garment where it can evaporate or move to the next layer away from the skin, channels of liquid movement through the inner hydrophobic Layer A must be created. Such channels ("wicking windows") can be created, for example, by needle punching or by hydroentangling techniques. In needle punching, those skilled in the art can select appropriate equipment and equipment set up. The equipment may be either rotary or flatbed. Variables such as needle type, size, spacing and machine speeds can be controlled to vary the amount or degree of needling and the penetration of Layer B through Layer A. Large needles may be used to create relatively large wicking channels in the fabric and produce a fabric with voids or small holes where the needles have been withdrawn from the substrate. Fibers from the hydrophilic Layer B can also be pushed through the hydrophobic Layer A to produce the channels or "wicking windows" which are actually bundles of hydrophilic fibers which serve as pathways of wicking.

The outer layer, Layer B, and the inner layer, Layer A, may each range in weight, for example, from about 1 oz./square yard to more than 20 oz./square yard. A more desirable range is about 1 to about 14 ounces per square yard for recreational performance apparel and about 0.1 to about 8.0 ounces per square yard for absorbent products such as cover stock or wipes. The optimum area density of each layer will depend on a number of factors, including the nature of the end product, intended end use or activity, environment, personal preferences and layering system (if any) used by the wearer.

By varying the relative area densities, constructions, types of fabrics (i.e. wovens, knits or nonwovens), methods of lamination or making the two or more layers into one, and the amount and nature of needling or hydroentangling, the design possibilities are many. As in the other embodiments, garments can be engineered to specific activities; environments; personal preferences and layering system (if any) of the wearer. Likewise, absorbent products, which are typically nonwovens, can be engineered with a broad range of properties.

Embodiment 5

Embodiment 5 involves using crosslinking as a means of reducing the absorbent capacity: Any of above embodiments or methods of producing recreational performance apparel from 100% cotton (or other cellulosic fibers) can be further enhanced or modified by including crosslinking resins applied in a continuous or discontinuous fashion. Crosslinking resins such as those used to produce wrinkle resistant cotton products (e.g., citric acid, maleic acid, DMDHEU, BTCA, other polycarboxylic acids such as polymaleic, etc.) can be used. Such treatment chemistries can be applied to fiber, yarn, fabric or garments. These materials will effectively reduce the absorbent capacity of regular (untreated) cotton by about 5 to 30% or more, depending on the chemistry used, the application amount, and the technique used (including curing), and the test method used for the absorbent capacity measurement. They can reduce the water that is held inside the fiber itself by bonding adjacent cellulose molecules and reducing the swelling of the fiber when it is exposed to a moist environment. Such crosslinking treatments do not necessarily eliminate wicking however, and therefore can be applied uniformly to the entire substrate as is common for wrinkle resist cotton apparel. Discontinuous means of application can also be used. These treatments provide the textiles with sufficient hydrophobicity to reduce the absorbent capacity of the treated substrate. These treatments may also provide the textiles with wrinkle resistance, smooth drying properties and durability to repeated laundering in alkaline detergents. The crosslinking treatments may include the use of a suitable catalyst (such as, for example, curing catalysts such as magnesium chloride, alkali metal hypophosphites, alkali metal phosphites, alkali metal polyphosphates, alkali metal dihydrogen phosphates, and many others) and/or the use of heat.

This technique can be used as a stand alone method (i.e., without the inclusion of other treatment chemistry such as fluorochemicals, silicones or waxes) for producing the recreational performance apparel. Alternatively, this technique may be used in conjunction with a hydrophobic treatment.

In this embodiment, light weight, thinner fabrics are preferred. Thinner fabrics have less absorbent capacity in general and hence will not get as heavy when wet and will dry faster than thicker fabrics. For example, area densities for recreational performance apparel in the range of about 1 to 8 oz./square yard are preferred, with area densities in the range of about 2 to 6 oz./square yard being more preferred. For cover stock (i.e. topsheets) used in absorbent products such as disposable diapers, much lighter fabrics are used, such as in the range of 18 grams per square meter.

Resins, as noted in this embodiment, will reduce absorbent capacity but allow wicking to be maintained. The resin may be applied before, after or in conjunction with the hydrophobic treatment. Resins and such hydrophobic treatments mentioned in these embodiments are both normally applied after dyeing. However, dying may be done subsequently for special or novelty effects.

Embodiment 6

Embodiment 6 involves garment treatments: As in Embodiment 3, garments may be printed, sprayed, dipped or otherwise treated to produce a discontinuous treatment. The discontinuous treatment allows many small channels or "wicking window" in the fabric from which the garment is made. Garment printing is a common technique. Since the durable hydrophobic chemistry can be chosen to be invisible, patterns do not need to be carefully aligned from front to back in the garment.

In a preferred embodiment, the print paste does not penetrate through the fabric. Garments may be turned inside out for treatment, so that only the side of the garment in contact with skin is treated. In this manner, one side of the garment is inherently more hydrophobic than the other.

A resist treatment may be used as described above in other embodiments (i.e., applied in a discontinuous manner by printing, spray, foam, etc.) such that the durable hydrophobic treatment chemistry can be applied to the whole garment by common garment dyeing and finishing techniques. In this case, the resist will keep the durable hydrophobic chemistry from attaching to the cotton fiber.

Any of the above embodiments may be used to tailor apparel for a variety of applications, activities, environments, or personal preferences of the wearer. The area density of fabrics for any of the above examples may vary, for example, from about 1 to about 30 oz./square yard. For a single layer warm weather activity the preferred range will be about 2 to 8 oz./square yard. For an outerwear garment for cold weather applications, the preferred weight range will be from about 4 to about 20 oz./square yard.

Any of the above methods can be used with blends of cotton and/or any hydrophilic fiber and/or a synthetic or any hydrophobic fiber such as polyester, polypropylene or nylon.

Any of the above garments may be used as a single layer or as one layer of a multi-layer system of dress, for example, for cold weather outdoor activities.

In each of the embodiments described above, preferably between 40 and 90% of the cotton fabric next to the skin remains dry. Preferably between 10 and 60% of the cotton fabric next to the skin is untreated, absorbent and wicks moisture away from the skin and into the outside of the fabric where it evaporates and cools, in a similar manner to an untreated garment.

The hydrophobic treatments in each of the embodiments can be attached to the cotton and/or other cellulosic fibers using any known methodology. Preferably, the methodology involves forming a covalent bond between the hydroxy groups on the cellulosic substrate and reactive functional groups (for example, hydroxyl, carboxylic, phosphoric, sulfonic or other acids, amines, halogens and the like) on the compounds to be attached. The hydrophobic treatment chemistry may itself contain crosslinking groups capable of producing durability by crosslinking to itself or directly to the cotton or other cellulosic or other hydrophilic fiber. Another option is that a separate crosslinking agent is used to bond the hydrophobic chemistry or any chemistry that can reduce the absorbent capacity of the hydrophilic fiber such as cellulose, to the cellulose.

Embodiments Related to Absorbent Products

Although the above embodiments specifically describe applications involving garments, the techniques, fibers, yarns, and fabrics described in the embodiments may also be used to make other articles of manufacture. These articles include, but are not limited to, absorbent products such as diapers and sanitary napkins.

Generally, diapers and sanitary napkins include a topsheet that is worn next to the user's skin and an absorbent core that is used to store bodily fluids such as urine and menstrual fluid. The topsheet has an inside surface for contacting the user's skin and an outside surface. The absorbent core is adjacent the outside surface of the topsheet. The absorbent core may be formed from any absorbent material such as, for example, hydrophillic fibers (such as cellulosic fibers), superabsorbent polymers, and mixtures thereof. As used herein, the absorbent core includes any acquisition layer between the final storage area (for bodily fluids) of the absorbent product and the topsheet.

The topsheet is typically a nonwoven and may have a predominantly hydrophobic inside (i.e., a topsheet that has a reduced absorbent capacity) and an outside that is predominantly absorbent. The topsheet may also be uniformly and predominantly hydrophobic from inside to outside, as long as it is designed to allow fluid to pass quickly through the topsheet and into the absorbent core.

The topsheet of such diapers and sanitary napkins may be composed, for example, of the following: (1) 100% cellulosic fibers; (2) a blend of cellulosic fibers and synthetic fibers such as polypropylene, polyester, or nylon; (3) a blend of cellulosic fibers which have been treated with a hydrophobic treatment and a synthetic fiber which has wicking properties; and (4) a blend of absorbent cotton (or other hydrophilic fiber) and cotton (or other hydrophilic fiber) which has been treated or processed to be hydrophobic. Cotton linters, comber, gin motes, shoddy, and various other lower cost cotton waste materials may be used as the source of cotton. The fibers used in the topsheet may be treated with any of the hydrophobic treatments described herein, such as, for example, application of silicones, waxes, fluorocarbons, zirconium compounds, oils, latexes, or crosslinking resins or agents including carboxylic acids and polycarboxylic acids such as citric, maleic, butane tetra carboxylic, or polymaleic acids. Blends of these hydrophobic treatment materials may also be used.

When cotton is used, the normal scouring and bleaching process which is used to purify and make cotton absorbent may be modified to allow the cotton to maintain the normal hydrophobic properties of raw cotton. This is done by not removing all of the natural cotton oils and waxes which are contained on the surface (cuticle) of the natural raw cotton (i.e., all or a portion of the natural oils and/or waxes on the fiber surface are maintained). For example, a normal scouring and bleaching process for cotton in a kier (i.e., a high pressure vessel) may comprise the following steps:

(1) Scour for approximately 50–60 minutes at about 265° F. and about 40 lb/in². In this step, the cotton fiber is placed into the kier and may be wetted out with warm water and surfactant if needed. The temperature and pressure of the kier is gradually brought to about 265° F. and about 40 lb/in$^2$ where it is held for approximately 50–60 minutes. The following mixture is circulated through the cotton fiber during this step:

3.5–5.5% NaOH (100% NaOH basis)
0.6–0.8% Surfactant/emulsifier
0.1–0.4% chelate (alkali stable).

The liquor to goods ratio in the kier is about 4:1 to 5:1 and the percentages are the percentages on weight of goods (OWG). At the end of the step, the cotton fiber is washed thoroughly with water.

(2) Bleach for approximately 30 minutes at about 230° F. and about 20 lb/in$^2$. In this step, the temperature and pressure of the kier is gradually brought to about 230° F. and about 20 lb/in$^2$ where it is held for approximately 30 minutes. The following mixture is circulated through the cotton fiber during this step:

0.6–1.2% organic stabilizer such as Dequest 2066 stabilizer from Monsanto
0.6–1.2% buffer such as sodium tripolyphosphate
0–0.4% NaOH (100% NaOH basis)
0–0.2% surfactant/wetting agent.

The liquor to goods ratio in the kier is about 4:1 to 5:1 and the percentages are the percentages on weight of goods (OWG). At the end of the second step, the cotton fiber is washed thoroughly with water and is acidified with 0.6–0.8% of 56% acetic acid on the last rinse.

This normal scouring and bleaching process can be modified to yield purified and bleached fiber without removing any or without removing all of the natural waxes and/or oils such that the cotton fiber maintains some or all of the hydrophobic properties of raw cotton (i.e., the fiber has a reduced absorbent capacity compared to normal scoured and bleached cotton fiber). According to the present invention, the modification of the normal scouring and bleaching process involves reducing the concentration of one or both of the base or the oxidizing agent, replacing the base and/or the oxidizing agents with other agents, reducing the time of one or both of the scouring or bleaching steps, and/or reducing the temperature in one or both of the scouring or bleaching steps. As an example, in the scouring and bleaching process described above, one or more of the following modifications could be used to leave all or some of the natural waxes and/or oils on the resulting bleached and purified cotton fibers: (1) the temperature of the scouring step could be reduced from 265° F. to 80° C.; (2) the NaOH used in the scouring step could be reduced to about 0.5% or less on weight of goods; (3) the NaOH could be replaced in the scouring and/or bleaching steps with sodium carbonate. An alternative means to maintain all or a portion of the natural oils and/or waxes on the cotton is by depositing on the fiber during the preparation process hard water salts or compounds or complexes containing hard water metals (e.g. calcium and magnesium) either alone or in combination with a variety of other materials including silicates or any of the hydrophobic treatment materials mentioned above. These modifications along with the times of treatment during each step may be adjusted as needed to achieve the desired level of purification and whitening as well as the desired level of absorbency/hydrophobicity. The resulting fibers may be used alone in a cellulosic substrate such as the topsheet of an absorbent product, may be blended with normal hydrophilic cotton (i.e., cotton that has been subjected to the normal scouring and bleaching process), or may be blended with synthetic fibers such as polypropylene that have hydrophilic or wicking properties.

When the top sheet is 100% cotton or other hydrophilic cellulosic fiber, the inside of the top sheet may be treated in a discontinuous manner with a hydrophobic treatment after the nonwoven web has been formed. The discontinuous hydrophobic treatment may be applied to the topsheet by printing, spraying, foaming, air lay powder or liquid deposition, dosing, coating, dripping, blowing, vacuum, water jets, plasma or hydroentangling devices. Because topsheets are often very thin and light weight (e.g. 18 grams per square meter), there will be rapid and complete penetration of the treatment to the opposite side of the web in some embodiments no matter which side of the topsheet is treated.

The top sheet may also be produced such that the entire top sheet is composed of 100% cotton (or other hydrophilic fiber or blends of cotton and synthetic fibers) which has been treated or processed such that all of the topsheet is hydrophobic or has a substantially reduced absorbent capacity. In such an embodiment, the top sheet may be an apertured nonwoven where the apertures function as "wicking windows" or channels for the flow of body fluids (e.g. urine, menstrual fluid, etc.) into the absorbent core of the end product. The size of the apertures preferably ranges from about 0.01 to about 10.0 millimeters. The spacing between the apertures preferably ranges from about 0.01 millimeters to about 10.0 millimeters and may be uniform or non-uniform. The apertures may be created by hydroentangling, air jets, water jets, or needle punching. The apertures may contain hydrophilic or wicking fibers from a second layer of the topsheet, from an adjacent nonwoven substrate, from an acquisition layer, or from the absorbent core. In such an embodiment, the hydrophilic fibers from the second layer, adjacent nonwoven substrate, acquisition layer, or absorbent core may be inserted or forced into the apertures of the topsheet by pressure, vacuum, laminating, air jets, or water jets. The hydrophilic wicking fibers from a second layer, an adjacent nonwoven substrate, an acquisition layer, or an absorbent core can serve to start the flow through the apertures and serve as wicking windows or channels of flow simply by the pressure exerted by the head of body fluid or the combination of the head of body fluid and skin contact.

In another embodiment, a hydrophilic synthetic fiber with wicking properties is blended with a hydrophobic cellulosic fiber (such as cotton) and made into a nonwoven web by carding, air lay, wet lay, Rando Webber, hydroentangling, thermal bonding, chemical bonding, needlepunching or any combination thereof. The hydrophilic synthetic fiber and the hydrophobic cellulosic fiber are predominantly on opposite sides of the nonwoven web, thus allowing one side to be predominantly hydrophobic (but still wick or readily pass body fluids) and the other side to be predominantly hydrophilic (to pull body fluids through the predominantly hydrophobic side of the web). The physical properties of the hydrophilic synthetic fiber and the hydrophobic cellulosic fiber may be significantly different to promote the migration of the two fibers to the opposite sides of the nonwoven web in the web manufacturing process. For example, the denier and/or staple length of the synthetic fiber and/or the micronaire and/or staple length of the cellulosic fiber may be used to promote the migration of the two fibers to opposite sides of the web in the web forming process. The hydrophilic synthetic fiber in this embodiment may also be replaced with hydrophilic cellulosic fiber, and both the hydrophobic fibers and the hydrophilic fibers may be cotton.

In yet another embodiment, the nonwoven topsheet is composed of two layers. One layer may be hydrophilic cellulosic or synthetic fiber (that will wick) and the second layer may be a hydrophobic cellulosic or synthetic fiber. The hydrophobic layer is to be worn next to the skin. The two layers may be formed and/or combined by any of the following means or combinations thereof: (1) bonding two nonwoven webs by chemical bonding, laminating, hydroentangling, air jets, thermal bonding using fibers, powder bonding, calendaring, needlepunching, air lay, wet lay, pressure or vacuum, or combinations thereof; (2) forming a first nonwoven web (by any conventional means) and subsequently or simultaneously depositing a second layer of fibers by air lay; wet lay; carding; blowing, vacuum, or combinations thereof; or (3) tandem carding, carding combined spun bonding, melt blowing, hydroentangling, or needlepunching. Wicking may be achieved through the hydrophobic layer during product use by any of the following means or combinations thereof: hydroentangling; air jets, water jet, pressure, vacuum; needle punching, or simply by using webs or layers in the web which are very thin (e.g., from 0.0001 millimeters to 2.0 millimeters) such that voids between fibers or holes exist in one or both of the layers to allow liquid to wick from the hydrophobic side to the hydrophilic side of the nonwoven web or webs.

The topsheet may be a blend of hydrophobic (or reduced absorbent capacity) fiber and hydrophilic fibers, with the ratio of the two fibers ranging from 1/99 to 99/1 depending on the absorbency and flow characteristics required for the end product.

Optional Components

Additional components can optionally be added to the fiber, yarn, fabric and/or garment compositions described herein. These include, but are not limited to, fire retardants, dyes, wrinkle resist agents, foaming agents, buffers, pH stabilizers, fixing agents, stain repellants such as fluorocarbons, soil repellants, wetting agents, softeners, water repellants, stain release agents, optical brighteners, emulsifiers, and surfactants.

Methods of Evaluating the Compositions

The suitability of the treatment compositions for an intended use will depend on the ability of the treated cellulosic substrate to pass various standard performance tests. Some examples of suitable performance tests are present in the Examples below, while others are known to those skilled in the art of manufacture of the type of end products noted above. Using these tests, with a suitably prepared composition, one can readily determine the efficacy of the composition for its intended use.

EXAMPLES

The compositions and methods described herein will be better understood with reference to the following non-limiting examples.

Example 1

Gross Absorbency (Absorbent Capacity) Study of Water on Fabric: Comparing Fluorocarbon Printed Fabric vs. Untreated 100% Cotton Control Fabric Summary Printing a fluorocarbon (FC)/resin formulation on a washed and prepared 100% cotton knit fabric significantly reduced the absorbent capacity (or total wet pick up) of the test fabric compared to an untreated control fabric.

The idea of printing a fluorocarbon (FC) with approximately 50% penetration on the back of 100% cotton knit fabric to reduce the overall water uptake (and therefore reduce the drying time and improve various other properties such as tendency to sag when wet or stick to the skin, etc.) was evaluated.

Introduction

Altering the properties of naturally high absorbing 100% cotton fabric to achieve lower water absorbency without sacrificing comfort and feel was the goal of this example. As determined in various publications: the drying time of a garment depends on the amount of water absorbed, not the fiber type.

Our previous work indicated that there was not a negative influence in respect to air breathability (Frazier) and moisture vapor transport (Mocon) when using FC on cotton fabric. Frazier and Mocon are two important factors closely related to the sensation of comfort.

Objective

The objective of this example was to develop a method for quantitative measurements of gross/total water absorbency on fluorocarbon (FC) printed fabric compared to an untreated control fabric. This method can be used to demonstrate that a targeted FC application effectively reduces the overall water uptake on 100% cotton fabric, subsequently reducing the drying time, but maintaining wicking characteristics.

Experimental

The fabric used for this study was 18 cut jersey, 16 singles, ring spun 100% cotton knit fabric SK-1499-2C. The fabric was received as greige fabric and prepared in the Dyeing and Finishing Research Lab (DFRL). The fabric was bleached and then acid neutralized in a Sclavos machine. The following steps were taken to prepare the fabric for printing.

Additional Scouring Step

A large swatch (approximately 2–3 yards) was cut from the bleached fabric roll then scoured and extracted in warm water in a regular washing machine. No detergent was added, but 80 g/80 L "Carbapon CDN" from "Clariant", which is a slightly acidic chemical formulation, was used to ensure complete removal of any residual detergents left behind from previous washing steps. The fabric was dried in a dryer for 60 minutes or until completely dry. Universal indicator was dropped on the dry fabric to check the pH. The resulting orange color indicated a pH of around 5.

Preparation for Printing

Four sample swatches were cut out, using a template measuring 17 inches×24 inches. This was the most suitable fabric size and large enough to be covered by the striped area of the print screen.

The synthetic print paste used for the experiment was "Imperon LV-5" in an 8% concentration in water. (Synthetic paste was preferred over the commonly used starch—ether paste since it required no after wash due to yellowing at the higher curing temperatures necessary for the fixation of the FC/resin system). The consistency of the paste was intentionally prepared to be of higher than normal viscosity. This enabled more FC formulation to be added to the paste (hence increasing the active fluorine level) without attenuation.

A formulation of Mitsubishi's FC "Repearl FC-35" in a 6% concentration and the resin "Repearl MF" in a 3% concentration on weight of bath (OWB) were mixed with the paste in a ratio of 1:1.5 (paste to formulation). To enhance the visibility of the paste, some blue dye (Tectilon Blue 4 RS KWL 200 and 5 g/200 ml water) was added.

Printing Setting

The individual sample swatches were labeled and the dry weight recorded. Each swatch was placed with the backside facing the screen on the printing table. After installing the stripe patterned print screen on top of the fabric, the metal rod and table settings were selected.

Settings: rod size=15 mm (largest), speed=20, polarity M=2 (1 is for small bars, 2 for large ones), passes=2, and magnet=6.

Printing was performed as follows:

After the screen and the metal rod were in place, the power switch was turned to position "1" (on). An approximately ½ to 1 inch thick layer of the now blue print paste was poured in front of the rod and the ←M→ switch turned to "2" which moved the bar to the right side of the screen. Upon completion the power was turned off, the rod lifted and placed so that the paste was in front of it to the left. The paste was replenished when necessary, the power turned back on and the ←M→ switch turned to the "1" position, moving the bar to the left. The last step concluded the printing procedure and the screen was lifted to remove the now blue striped printed fabric. The wet weight was recorded and the fabric was put on a hanger. The other swatches were finished the same way and put in a Sussman garment oven to dry at 230° F. (110° C.) for 20 minutes. They were then immediately cured at 338° F. (170° C.) for 3 minutes.

Gross Absorbency Measurements

The gross absorbency trials were performed on fabric 20/1, which had a wet pickup (WPU) of 56.85% (print paste with FC). The fabric was cut in half. A test series was conducted on half of the fabric right after printing. The other half was subjected to one home laundering (HL) using warm water and liquid Tide and then dried in a garment oven. A small fabric piece of the unlaundered and home laundered (HL) swatches were sent to a testing lab for fluorine analyses.

Each fabric half was tested in seven replicate tests. The sponge size was 4.5 inches×8.0 inches×3.0 inches, with a surface area of 8.0 inches×4.5 inches. To be able to place two swatches (one control, one printed) on the sponge surface, each sample was cut out to be 4.0 inches×3.0 inches, which was equal to 24 blue stripes per sample.

Test Set Up

An aluminum dish measuring 12.5 inches (L)×10.5 inches (W)×4.5 inches (H) was filled with cold tap water.

One of the two fine pore sponges, brand "Armaly, Big Blue Wash Sponge," was thoroughly wetted under running tap water. It was then placed in the middle of the aluminum dish and enough water added to have the sponge completely saturated and the water level up to approximately ¼ of an inch below the sponge surface. The other dry sponge was completely wrapped in aluminum foil, leaving a non-absorbing but smooth and even surface at the bottom. The weight of that sponge was 59.82 grams.

A piece of "Armaly, chamois drying cloth" covering exactly the surface area of the sponge (8.0 inches×4.5 inches) was pre-saturated with water as well and placed on top of the sponge in the dish. The purpose of the cloth was to present a uniformly wet surface area, ensuring even water absorbency of the samples.

Prior to testing all 4×3 inch swatches (printed and controls) were labeled and weighed. The FC printed swatch was then placed with the blue striped side (back of fabric) on the wet sponge. The untreated control was added next to it (backside on sponge) and they were both covered with the dry aluminum foil wrapped sponge, functioning as a weight to keep the fabric from curling.

The time until complete saturation of the printed fabric was noted. The wet samples were then, one at a time, transferred into a small pre-weight plastic dish and weighed on a top loading balance to determine the wet pick up. All sample swatches, including the home laundered ones, were processed this way.

Note: The water level in the dish had to be monitored and adjusted due to the diminishing water readily absorbed by the fabrics. The sponge, as well as the cloth, was rinsed after several series to remove possible contamination of excess print paste, etc. (especially for the unwashed samples).

Results and Discussion

TABLES I and II give a detailed overview of the water wet pick up values observed on the unlaundered printed fabrics including the control fabrics.

TABLE I

% WPU Values of FC Printed Fabrics (no HL)

| Sample ID | Dry Fabric Weight in Grams | Wet Fabric Weight in Grams | % WPU[1] | Time Until Saturation | % less H$_2$O Absorbed vs. Control[2] |
|---|---|---|---|---|---|
| #1 | 1.57 | 5.38 | 242.7 | 20 minutes | 55.3% |
| #2 | 1.57 | 5.33 | 239.5 | 30 minutes | 66.8% |
| #3 | 1.62 | 5.45 | 236.4 | 60 minutes | 63.7% |
| #4 | 1.59 | 5.76 | 262.3 | 20 minutes | 54.4% |
| #5 | 1.58 | 5.54 | 250.6 | 16 minutes | 60.4% |
| #6 | 1.59 | 5.63 | 254.1 | 15 minutes | 64.3% |
| #7 | 1.58 | 5.58 | 253.2 | 30 minutes | 58.2% |

Note: [1]% WPU = (wet weight × 100\dry weight) − 100
[2][% WPU (control) × 100\% WPU (FC printed)] − 100

The saturation times were determined by periodically checking on the samples until they were wet out completely.

TABLE II

% WPU Values of Untreated Controls (no HL)

| Sample ID | Dry Fabric Weight in Grams | Wet Fabric Weight in Grams | % WPU |
|---|---|---|---|
| #1 | 1.60 | 7.63 | 376.9 |
| #2 | 1.62 | 8.09 | 399.4 |
| #3 | 1.60 | 7.79 | 386.9 |
| #4 | 1.60 | 8.08 | 405.0 |
| #5 | 1.63 | 8.18 | 401.9 |
| #6 | 1.61 | 8.33 | 417.4 |
| #7 | 1.62 | 8.11 | 400.6 |

The control fabric was always subjected to the same conditions as the FC printed samples. For example, the control test swatch was dried and cured at the same temperature as the printed fabric. Further, it was left on the wet sponge until the printed swatch was completely saturated. FIG. 1 shows a graphical display of the WPU values of FC printed vs. untreated control fabric before one home laundering (HL). TABLES III & IV give the absorbency results of the fabrics tested after 1 HL with Tide.

TABLE III

% WPU of FC Printed Fabric after 1 HL

| Sample ID | Dry Fabric Weight in Grams | Wet Fabric Weight in Grams | % WPU | Time Until Saturation | % Less H$_2$O Absorbed vs. Control |
| --- | --- | --- | --- | --- | --- |
| #1 | 1.52 | 5.38 | 253.9 | 10 minutes | 52.9 |
| #2 | 1.52 | 5.47 | 259.9 | 10 minutes | 45.8 |
| #3 | 1.56 | 5.52 | 253.8 | 10 minutes | 47.4 |
| #4 | 1.55 | 5.57 | 259.4 | 10 minutes | 46.4 |
| #5 | 1.53 | 5.47 | 257.5 | 12 minutes | 52.4 |
| #6 | 1.54 | 5.31 | 244.8 | 6 minutes | 61.1 |
| #7 | 1.55 | 5.33 | 243.9 | 10 minutes | 59.4 |

TABLE IV

% WPU of Control Fabrics after 1 HL

| Sample ID | Dry Fabric Weight in Grams | Wet Fabric Weight in Grams | % WPU |
| --- | --- | --- | --- |
| #1 | 1.59 | 7.76 | 388.1 |
| #2 | 1.61 | 7.71 | 378.9 |
| #3 | 1.63 | 7.73 | 374.2 |
| #4 | 1.62 | 7.77 | 379.6 |
| #5 | 1.61 | 7.93 | 392.5 |
| #6 | 1.61 | 7.96 | 394.4 |
| #7 | 1.59 | 7.77 | 388.7 |

Figure 2:
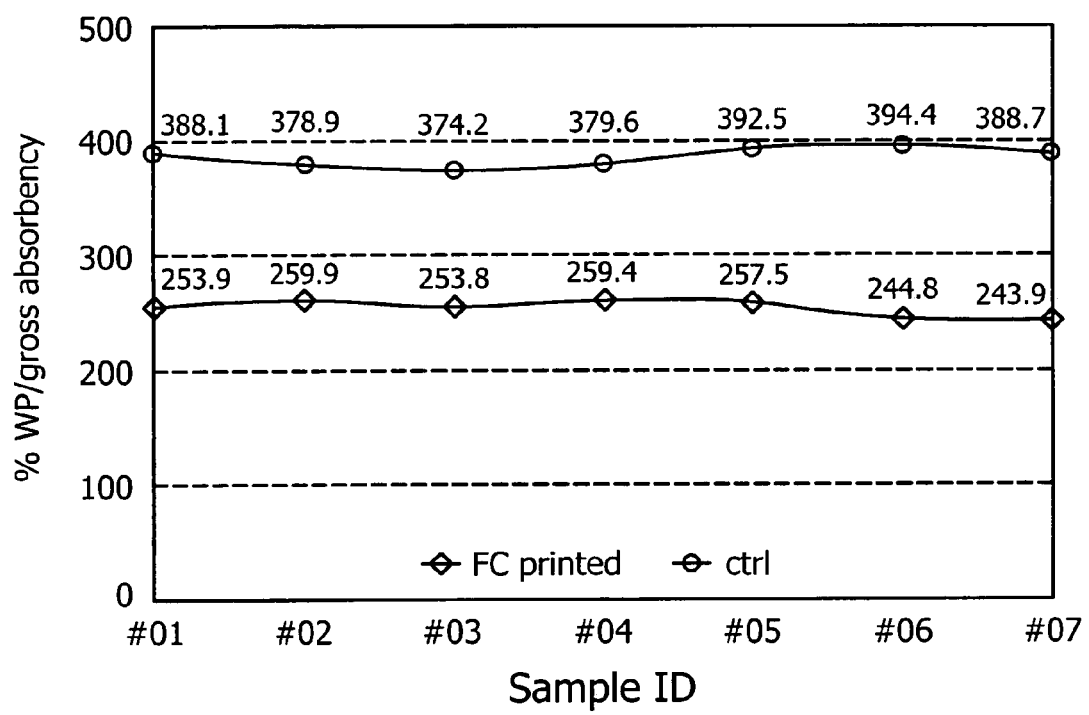
FIG. 2 is a graph showing the percent wet pickup of water (wt. percent/gross absorbency) for various treated samples in Example 1 after one home laundering.

FIG. 2 shows a graphical display of the gross absorbency after 1 HL.

Figure 3:
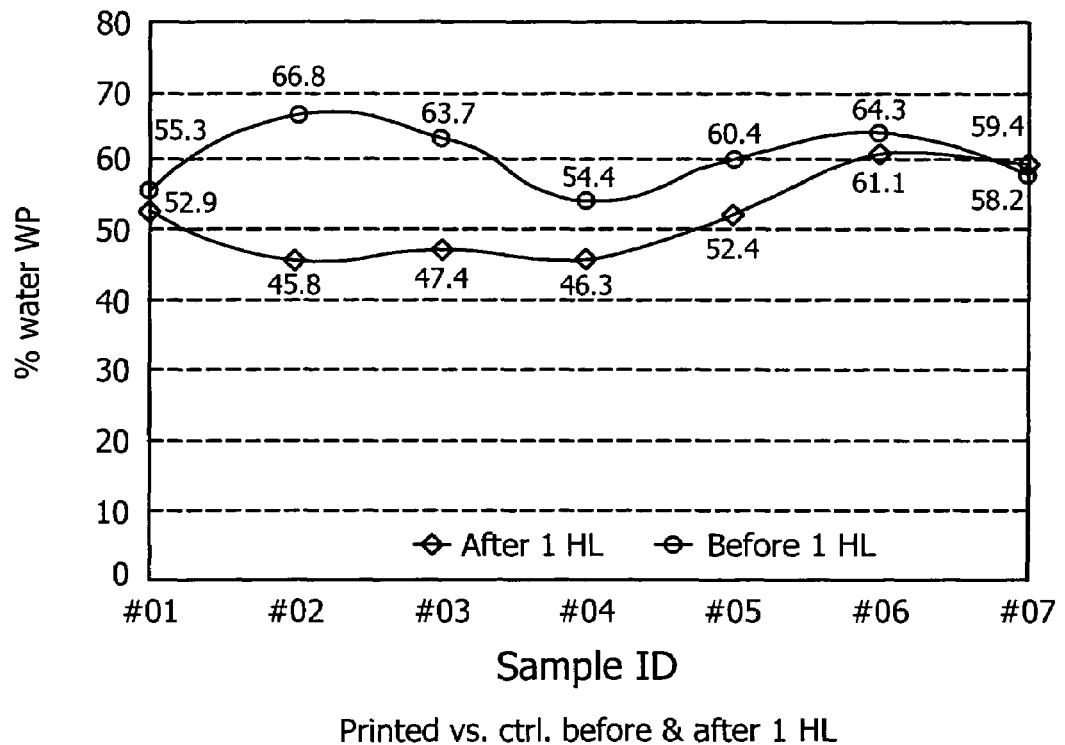
FIG. 3 is a graph showing the percent wet pickup of water (percent water by wt. percent) for various treated samples in Example 1, versus control, before and after one home laundering.

FIG. 3 shows the % less water absorbed related to the corresponding controls of the printed fabrics before and after 1 HL.

Fluorine test results of the printed fabrics (unwashed and washed) are given in TABLE V. The samples were analyzed in duplicate using the same sample size and number of stripes.

TABLE V

Fluorine Test Results Before & After 1 HL

| Sample ID | % Fluorine |
| --- | --- |
| 20/1 unwashed | 0.23 |
| 20/1 washed | 0.23 |

Summarized Results

The FC proved to be durable and fixed since the fluorine values before and after 1 HL remained the same. (A concentration of at least 0.23% active fluorine is recommended). See TABLE V.

The gross absorbencies of the untreated controls were insignificantly lower after 1 HL compared to the first series, probably due to minimal shrinkage of the fabric after washing and drying. See TABLES II & IV.

The water repellency of the printed fabrics was to be observed by the dry, blue striped area on the back of the fabric. The face of the fabric was wet and absorbent.

The FC printed samples had distinct lower water WPU values before & after HL compared to the untreated controls. The prolonged and irregular saturation times of the unwashed printed fabrics were most likely caused by migrated print paste, which should be readily overcome by improving the paste formulation. This seems to be the most logical explanation since the samples absorbed readily after 1 HL. See TABLES I to IV.

Conclusions

To validate the FC durability it is necessary to conduct a brief home laundering study. Testing the printed fabric after 10 and up to 50 HL for fluorine should give an indication of the fixation and the general influence of repeated detergent exposure to the FC performance.

Example 2

Moisture Regain of FC Treated vs. Untreated 100% Cotton Fabric

Summary

A fluorocarbon (FC) application does not affect the moisture regain of 100% cotton fabric. The amount of moisture a fabric absorbs is related to its environment: the higher the humidity, the higher the moisture regain.

Introduction

This experiment was designed to develop a fabric construction/chemical treatment that reduces the water absorbency of 100% cotton fabric. The objective was to determine the influence of a FC treatment on the natural moisture regain of 100% cotton fabric.

Experimental

Fabrics from previous trials were used for this brief study. A 100% cotton blue T-shirt from Hanes® as well as a swatch of a white "beefy" T-shirt from Hanes® were used as untreated control fabrics. FC treated samples were pieces of an olive 100% cotton shirt from K-Mart® sprayed with Mitsubishi's 6% "Repearl®F 35" and 3% "Repearl®MF" on the back of the shirt at 100% WPU ("B in 100"). The second FC treated sample was a "beefy" T-shirt printed with the same FC as mentioned above in 3% Repearl®F 35/1.5% Repearl® MF concentration in stripe pattern (covering approximately 50% of the fabric surface).

Experimental Set Up

Each fabric was measured in duplicate. Sample swatches were cut out with a weight between 8–10 grams, put into labeled glass weighing bottles and dried in a forced air oven at 105° C. for 24 hours. The weighing bottles were cooled in a desiccator for ½ hour and the individual sample weights recorded on an analytical balance. The actual moisture regain process was conducted at the fiber processing center (FPC) in a conditioned environment: the fabrics were removed from the bottles and placed on a table for 4 hours to regain the previously expelled moisture. Meanwhile, the weighing bottles were dried and cooled and while in the desiccator, transported to the location of the fabrics. The fabric samples were picked up and quickly added to the according bottles, sealed with a glass cap and put back in the desiccator for weighing. The difference in weight was noted which translated to the amount of moisture picked up by the fabrics.

Note: This test was repeated twice on different days and the room humidity and temperature recorded.

The following TABLES VI & VII give an overview of the test results:

TABLE VI

Moisture Regain after 4 hours at 74.3° F./47.2% relative humidity

| Sample ID | % Moisture Regain |
| --- | --- |
| blue Hanes ctrl. (untreated) | 6.44 |
| white "beefy" shirt ctrl. (untreated) | 6.07 |
| olive shirt "B in 100" (FC sprayed) | 5.99 |
| FC printed cotton ctrl. fabric | 6.16 |

TABLE VII

Moisture Regain after 4 hours at 75.4° F./56.2% relative humidity

| Sample ID | % Moisture Regain |
| --- | --- |
| blues Hanes ctrl. (untreated) | 7.20 |
| white "beefy" shirt ctrl. (untreated) | 6.88 |
| olive shirt "B in 100" (FC sprayed) | 6.87 |
| FC printed cotton ctrl. fabric | 6.92 |

Results and Discussion

FC treatment does not negatively influence the moisture regain of a fabric as can be seen in TABLES VI & VII. The percent of moisture a fabric absorbs is related to its environment, here the relative humidity. The higher the relative humidity, the higher the moisture regain of a fabric. (see FIGS. 1 & 2)

Example 3

Fluorocarbon Comfort Study for a Preliminary Wear Trial on 100% Cotton T-shirts

Summary

Four solid colored 100% cotton T-shirts were purchased at K-Mart®. The goal of this example was to use fluorocarbon treatments to make cotton hydrophobic and therefore reduce or partially eliminate the natural high water retention of cotton.

All four T-shirts were home laundered (HL) with AATCC detergent once to remove any impurities and topical softeners and dried in a regular dryer. Mitsubishi's fluorocarbon (FC) "Repearl® F-35" in conjunction with their formaldehyde free resin "Repearl® MF" were used for this evaluation.

Spray applications of the FC/resin formulation were targeted for a 20% wet pickup (WP) on the inside of T-shirt #1, 20% WP on the outside of shirt #2, 100% WP on the inside of shirt #3 and 100% WP on the outside of shirt #4. They were dried/cured and given to a volunteer for wear trial for strenuous exercise.

All four T-shirts resulted in the same performance of feeling extremely hot and uncomfortable due to the non-absorbing cotton. One positive effect noticed were the soft hand and an apparent "antimicrobial effect" (subdued odor) of this formulation.

The shirt with the 100% WV outside was additionally submitted to an enzyme/stone wash to simulate chemical/physical abrasion in an attempt to partially remove the FC. Subsequent absorbency and wicking tests proved this was not an effective means of achieving some increase in hydrophilic properties of the fully treated garment.

Furthermore, Frazier breathability tests indicated no negative influence of the FC application compared to an untreated T-shirt. Within the same brand (here, Hanes®) it even increased the air permeability. This phenomenon led to the conclusion that the "evaporative cooling" effect is probably the primary reason for a feel of comfort during exercise.

Mocon moisture vapor transmission tests resulted in higher values for two of the sprayed T-shirts compared to an untreated "Hanes" control.

Introduction

Polypropylene, nylon and polyester are the domineering synthetic fibers for the athletic wear market. Various fabric and fiber constructions and the application of wicking agents to enhance faster moisture transport away from the body make them appealing for active wear. Garments made from those fibers are lightweight and extremely fast drying, due to the synthetic properties of the fibers of not absorbing moisture.

100% cotton fabrics, on the other hand, supply a very nice "feel" to the skin, but absorb all moisture/sweat present (due to the porosity and molecular structure of cellulose) and therefore become saturated and very heavy. That results in prolonged drying times, discomfort and a "clammy" feeling.

Objective

The goal of this example was to reduce the natural absorbency of cotton by either complete or partial FC treatment of a fabric for example, to "seal" the cotton fibers to make them hydrophobic.

Since fluorocarbons are primarily used for raingear and to make fabrics water repellent, a combination of FC/resin that would act as a crosslinker to ensure permanent bonding to the cellulose molecule was tested in the following described spray application.

Experimental

Four solid colored 100% cotton T-shirts purchased at a K-Mart (brands were: three Hanes® and one Route 66®. all in size large) were thoroughly washed in a washing machine using AATCC standard laundry detergent to remove any softeners and dried in a dryer. Each shirt was labeled and the weight recorded before and after treatment to determine the actual wet pickup (WP). The treatment was performed as a spray application, using a formulation of 6% Repearl F-35 (on weight of bath OWB) which is a fluorocarbon manufactured by Mitsubishi and 3% (OWB) of their formaldehyde free crosslinker Repearl MF.

The T-shirts were labeled as follows:
1 "A out 100"
2 "B in 100"
3 "C out 20"
4 "D in 20"

"In/out" stands for inside/outside treatment of the shirt; the number indicates the target WP.

The actual wet pickup (WP) values are given in Table VIII.

TABLE VIII

Wet pick up values

| Sample ID | Target WP | Actual WP |
| --- | --- | --- |
| A out 100 | 100% | 101.37 |
| B in 100 | 100% | 99.02 |
| C out 20 | 20% | 28.61% |
| D in 20 | 20% | 32.24% |

The shirts were dried on hangers at 220° F. for about 15 min. or until dry and cured in a Sussman garment oven at 338° F. for 2 min. An absorbency test resulted in no water absorbency even after 10 min.

All four T-shirts were given to a volunteer for a one time wear trial during regular gym workouts. Three of the treated plus one untreated T-shirt as a control were also submitted for Mocon testing. Results are given in Table IX.

TABLE IX

Mocon Test Data

| Sample ID | Untreated | Average | FC treated | Average |
|---|---|---|---|---|
| untreated control; dark blue "Hanes" T-shirt | 1748 1765 | 1756.5 | / | / |
| "B in 100" olive Hanes T-shirt 1 HL | Not tested | / | 1612 1637 | 1624.5 |
| "D in 20" Route 66 shirt | Not tested | / | 2033 1970 | 2001.5 |
| "A out 100" Hanes shirt | Not tested | / | 2067 2021 | 2044 |

Frazier air permeability tests on four T-shirts were conducted. The following Table X gives an overview of the obtained data.

TABLE X

Frazier Air Breathability Values

| Sample ID | Air permeability value |
|---|---|
| Hanes dark, blue control | 83.95 |
| Hanes olive "B in 100" | 93.73 |
| Hanes "A out 100" | 96.18 |
| Route 66 "D in 20" | 76.16 |

After completion of the wear trial, shirt "A" (100% outside) was submitted to an enzyme/stone wash to simulate chemical/physical abrasion.

Enzyme Treatment

The chemical "abrasion procedure" involved an enzyme treatment using the Unimac rotary dyeing machine in the finishing lab. The liquor ratio was 10:1 and buffer A solution (3 g/l) and T-shirt were added at room temperature. The water temperature was then subsequently raised to 135° F. and the pH monitored to be between 4.5 to 5.0.

Colase CRC (2 g/l) was used as an enzyme and run for 30 min., then dropped and the shirt rinsed with hot water at 160° F. for 10 min.

The subsequent stone wash was performed as follows:

Stone Wash

The wet shirt was moved from the Unimac to a 50 lb. garment washing machine to perform the stone wash. The machine was loaded with 5 lb. fabric plus an equal amount of stones and run with water at room temperature for 45 min. All stones were removed before the extraction and an additional rinse cycle at 120° F. A regular dryer was used to dry the shirt.

Absorbency/Wicking Tests

A quick water absorbency test was conducted in several areas on all 4 shirts to check the water repellency and the uniformity of the FC. Since all 4 fabrics were extremely hydrophobic on both sides (face and back) it was unnecessary to test the wickability.

Results and Discussion

All FC spray applications penetrated the fabrics completely and exhibited more "raincoat" like properties on the shirts than anything else, but had a very soft hand. It was noted that all felt extremely uncomfortable during exercise due to the fact that all the moisture, sweat and heat retained close to the body.

Since all or most of both sides of the shirts were very water repellent, neither one would show any dark sweat spots from moisture being absorbed. One of the main reasons for experiencing a "clammy" feeling can probably be attributed to the lack of "evaporate cooling," prohibited by the non-absorbing FC.

Frazier breathability tests were conducted, performed on the worn and on one, one-time washed shirt, showed no negative influence of the FC on the "air flow" of the test samples. The treated shirts of the same brand (Hanes) had even higher air permeability values than the untreated control. Neither chemical nor physical abrasion resulted in any surface damage of the treated fabric to re-establish absorbency.

Mocon moisture vapor transmission tests revealed slightly higher numbers for two of the FC treated T-shirts compared to the untreated control.

Example 4

Drying Rate Study of Cotton vs. Synthetic Fabrics (Unimac Washing Machine)

Summary

100% cotton fabrics printed with a fluorocarbon (FC) have the same or faster drying rate compared to 100% polyester synthetic fabric. Test results within the four different Nike® fabrics representing synthetics used for athletic wear gave variations in initial percent WPU after Unimac extractions for two of the samples, possibly due to the construction of the fabric.

Objective

The goal of this brief study was to obtain some data that would support or refute the claim of synthetics drying faster because of their inability to absorb any water at all. One issue was whether FC-treated cotton fabric has a similar drying time to 100% synthetics.

Experimental

The study was laid out as follows:

Preparation of 100% Cotton Fabric

100% cotton "beefy" T-shirts from Hanes® were home laundered with liquid Tide® prior to treatment, dried and front and the back was cut out. The individual swatches were labeled in sets of two for each duplicate to be printed with a FC print paste a) on the face and b) on the back of one fabric. The print formulation consisted of a 1:1 ratio of the synthetic print paste mixed with a FC solution of 2% FC (Mitsubishi's "Repearl® FC 35") with 1% resin (Mitsubishi's "Repearl® MF") on weight of the bath (OWB).

The print settings were:

| rod size: 8 mm | speed: 40 |
|---|---|
| M: 1 | 1 pass/side |
| Magnet: 3 | |

All fabrics were weighed before and immediately after printing to obtain Wet Pick Up (WPU) values (see TABLE XI for details). After recording the WPU, the printed samples were put on hangers, dried at 220° F. for 20 minutes in a Sussman garment oven and cured for 2 minutes at 338° F.

TABLE XI

WPU values of FC printed samples

| Sample ID | % WPU |
|---|---|
| 4/1 Front | 28.07 |
| 4/1 Back | 26.66 |
| 4/2 Front | 27.67 |
| 4/2 Back | 25.97 |
| 4/3 Front | 27.12 |
| 4/3 Back | 27.32 |
| 4/4 Front | 27.75 |
| 4/4 Back | 26.15 |
| 4/5 Front | 25.00 |
| 4/5 Back | 18.93 |

Preparation of the Synthetic Fabrics

The synthetic fabrics selected for the trial were all supplied by Nike® and are listed in TABLE XII.

TABLE XII

Synthetics Sample ID

| Sample ID | Fiber ID |
|---|---|
| # IM 19537 white | 100% polyester |
| # IM 32994 red | 100% polyester |
| Olive fabric | 100% polyester |
| Yellow fabric | 100% polyester |

General Testing of Samples

The FC printed 100% cotton fabrics as well as the 100% polyester fabrics were all cut out to have the same weight of 27 grams per sample swatch. Each fabric was labeled, weighed on a top loading balance and tested in duplicate. The "wetting out" process was performed in the Unimac washing machine by adding one swatch of each duplicate set of six test fabrics (4 synthetics, 1 FC printed cotton, 1 untreated cotton ctrl.) to the machine, washing them for 5 minutes at 90° F. (just water) and extraction at full spin cycle speed for 2 minutes. The individual wet samples were then weighed again to determine the amount of water picked up and transferred on hangers to the fiber processing center (FPC for a conditioned environment) to record the weight loss in 15 minute increments over a 2 hour time period. The Unimac process was repeated on the other duplicate set of fabrics as well.

The following tables and graphs display the test data.

TABLE XIII

% Remaining Water on Sample # IM 19537 (duplicate testing)

| Time intervals in minutes | % water on fabric |
|---|---|
| 0 | A) 68.55 |
|   | B) 78.15 |
| 15 | 50.43 |
|   | 62.21 |
| 30 | 40.4 |
|   | 50.4 |
| 45 | 30.83 |
|   | 44.89 |
| 60 | 16.96 |
|   | 34.06 |

TABLE XIII-continued

% Remaining Water on Sample # IM 19537 (duplicate testing)

| Time intervals in minutes | % water on fabric |
|---|---|
| 75 | 7.17 |
|   | 4.86 |
| 90 | 1.20 |
|   | 6.05 |
| 105 | 0.69 |
|   | 6.67 |
| 120 | 0.58 |
|   | 0.54 |

TABLE XIV

% Remaining Water on Sample Yellow Nike (duplicate testing)

| time intervals in minutes | % water on fabric |
|---|---|
| 0 | 48.62 |
|   | 52.64 |
| 15 | 34.09 |
|   | 39.75 |
| 30 | 24.78 |
|   | 31.53 |
| 45 | 18.22 |
|   | 24.69 |
| 60 | 7.86 |
|   | 14.73 |
| 75 | 1.01 |
|   | 7.05 |
| 90 | B) 1.35 |
| 105 | B) 0.65 |
| 120 | DRY |

TABLE XV

% Remaining Water on olive Nike fabric (duplicate testing)

| time intervals in minutes | % water on fabric |
|---|---|
| 0 | 116.16 |
|   | 140.04 |
| 15 | 92.72 |
|   | 109.82 |
| 30 | 77.93 |
|   | 92.39 |
| 45 | 65.29 |
|   | 80.94 |
| 60 | 47.46 |
|   | 60.76 |
| 75 | 33.95 |
|   | 45.25 |
| 90 | 20.87 |
|   | 27.50 |
| 105 | 9.60 |
|   | 11.45 |
| 120 | 1.67 |
|   | 2.36 |

TABLE XVI

% Remaining Water on Sample # IM 32994 (duplicate testing)

| time intervals in minutes | % water on fabric |
|---|---|
| 0 | 145.78 |
|   | 96.63 |
| 15 | 130.58 |
|   | 86.81 |
| 30 | 123.16 |
|   | 81.20 |

TABLE XVI-continued

% Remaining Water on Sample # IM 32994 (duplicate testing)

| time intervals in minutes | % water on fabric |
|---|---|
| 45 | 115.78 |
|  | 74.02 |
| 60 | 103.56 |
|  | 65.87 |
| 75 | 95.02 |
|  | 60.43 |
| 90 | 84.76 |
|  | 54.71 |
| 105 | 75.78 |
|  | 46.20 |
| 120 | 66.91 |
|  | 38.37 |

TABLE XVII

% Remaining Water (average face & back) on Fabric 4/1

| Time Intervals in Minutes | % Water on Fabric |
|---|---|
| 0 | 30.43 |
| 15 | 20.26 |
| 30 | 13.93 |
| 45 | 8.07 |
| 60 | 5.01 |
| 75 | 3.70 |
| 90 | 2.66 |
| 105 | 2.40 |
| 120 | 2.30 |

TABLE XVIII

Remaining Water (average face & back) on Fabric 4/2

| Time Intervals in Minutes | % water on Fabric |
|---|---|
| 0 | 29.62 |
| 15 | 17.12 |
| 30 | 11.08 |
| 45 | 5.92 |
| 60 | 3.49 |
| 75 | 2.70 |
| 90 | 2.63 |
| 105 | 2.33 |
| 120 | 2.21 |

TABLE XIX

% Remaining Water (average face & back) on Fabric 4/3

| Time Intervals in Minutes | % Water on Fabric |
|---|---|
| 0 | 31.48 |
| 15 | 20.28 |
| 30 | 14.96 |
| 45 | 10.29 |
| 60 | 7.23 |
| 75 | 5.21 |
| 90 | 3.91 |
| 105 | 3.05 |
| 120 | 2.51 |

TABLE XX

% Remaining water (average face & back) on fabric 4/4

| Time Intervals in Minutes | % Water on Fabric |
|---|---|
| 0 | 32.41 |
| 15 | 20.66 |
| 30 | 16.22 |
| 45 | 10.59 |
| 60 | 7.01 |
| 75 | 4.89 |
| 90 | 3.43 |
| 105 | 2.67 |
| 120 | 2.45 |

Results and Discussion

Despite the limited number of samples tested, there seems to be a strong indication that printing a FC on 100% cotton fabric does indeed reduce the overall water uptake. This results in even faster drying times for treated 100% cotton than for some of the synthetics. Interestingly, it seems that not all synthetics absorb and dry at the same rate, but that fabric thickness and construction apparently are also important factors.

Variations of initial % WPU values after the "wetting out" process in the Unimac can be observed within the different 100% polyester fabric sets. Fluctuations are less noticeable for synthetic fabrics and yellow polyester. The % WPU values for the FC printed 100% cotton fabrics were also very reproducible and did not deviate a lot within data sets.

Modifications and variations of the methods and compositions described above will be obvious in view of the description of the invention. Such modifications are intended to be within the scope of the claims.

What is claimed is:

1. A woven or knit fabric comprising:
   an inside surface comprising cellulosic fibers; and
   an outside surface comprising cellulosic fibers;
   wherein:
   the inside surface has a discontinuous hydrophobicity, the outside surface has a higher absorbent capacity than the inside surface, and the fabric has channels of hydrophilic fibers for wicking liquid contacting the inside surface of the fabric to the outside surface of the fabric;
   the inside surface comprises a first yarn formed from a blend of cellulosic fibers treated with a hydrophobic treatment and cellulosic fibers not treated with a hydrophobic treatment; and
   the outside surface comprises a second yarn formed either from cellulosic fibers not treated with a hydrophobic treatment or from a blend of cellulosic fibers treated with a hydrophobic treatment and cellulosic fibers not treated with a hydrophobic treatment, the ratio of treated fibers to untreated fibers in the second yarn being lower than the ratio of treated fibers to untreated fibers in the first yarn.

2. The fabric of claim 1 wherein the ratio of treated fibers to untreated fibers in the first yarn is from 99:1 to 10:90.

3. A woven or knit fabric comprising:
   an inside surface comprising cellulosic fibers; and
   an outside surface comprising cellulosic fibers;

wherein:
the inside surface has a discontinuous hydrophobicity, the outside surface has a higher absorbent capacity than the inside surface, and the fabric has channels of hydrophilic fibers for wicking liquid contacting the inside surface of the fabric to the outside surface of the fabric;
the inside surface comprises a first yarn and a second yarn, the first and second yarns being formed from cellulosic fibers, the first yarn being treated with a hydrophobic treatment, the second yarn not being treated with a hydrophobic treatment; and
the outside surface comprises the first yarn and the second yarn, the first yarn being present on the outside surface of the fabric in a lower amount than on the inside surface of the fabric.

4. The fabric of claim 3 wherein the first yarn has been subjected to a discontinuous hydrophobic treatment.

5. The fabric of claim 3 wherein the ratio of the second yarn to the first yarn on the outside surface is from 99:1 to 10:90.

* * * * *